United States Patent
Maria de Peppo

(10) Patent No.: US 10,214,714 B2
(45) Date of Patent: Feb. 26, 2019

(54) PERFUSION BIOREACTOR

(71) Applicant: NEW YORK STEM CELL FOUNDATION, INC., New York, NY (US)

(72) Inventor: Giuseppe Maria de Peppo, New York, NY (US)

(73) Assignee: New York Stem Cell Foundation, Inc., New York, NY (US)

( * ) Notice: Subject to any disclaimer, the term of this patent is extended or adjusted under 35 U.S.C. 154(b) by 417 days.

(21) Appl. No.: 14/959,950

(22) Filed: Dec. 4, 2015

(65) Prior Publication Data
US 2016/0194593 A1 Jul. 7, 2016

Related U.S. Application Data

(63) Continuation-in-part of application No. PCT/US2014/072579, filed on Dec. 29, 2014.

(60) Provisional application No. 62/087,614, filed on Dec. 4, 2014, provisional application No. 61/921,915, filed on Dec. 30, 2013.

(51) Int. Cl.
  C12M 1/00 (2006.01)
  C12M 1/12 (2006.01)
  C12M 3/00 (2006.01)

(52) U.S. Cl.
  CPC ............ C12M 29/10 (2013.01); C12M 21/08 (2013.01); C12M 23/46 (2013.01); C12M 25/14 (2013.01)

(58) Field of Classification Search
  CPC ...... C12M 29/10; C12M 21/08; C12M 23/46; C12M 25/14
  See application file for complete search history.

(56) References Cited

U.S. PATENT DOCUMENTS

| | | | |
|---|---|---|---|
| 5,899,939 A | 5/1999 | Boyce et al. |
| 6,143,293 A | 11/2000 | Weiss |
| 6,472,202 B1 | 10/2002 | Banes |
| 8,398,714 B2 | 3/2013 | Boiangiu |
| 8,895,046 B2 | 11/2014 | Xuenong et al. |
| 8,926,699 B2 | 1/2015 | Burkinshaw |
| 2003/0100107 A1 | 5/2003 | Peschle |
| 2006/0257447 A1 | 11/2006 | Hinds et al. |

(Continued)

FOREIGN PATENT DOCUMENTS

WO  WO 1996/040002 A1  12/1996
WO  WO 1999/048541 A1  9/1999

(Continued)

OTHER PUBLICATIONS

International Search Report dated Aug. 22, 2016, regarding PCT/US2016/025601.

(Continued)

*Primary Examiner* — Gautam Prakash
(74) *Attorney, Agent, or Firm* — DLA Piper LLP (US)

(57) ABSTRACT

In some embodiments the present invention provides perfusion bioreactors and cell culture scaffolds suitable for the preparation of tissue grafts, such as bone tissue grafts. In some embodiments, the perfusion bioreactors comprise a graft chamber and/or a graft chamber insert configured to hold a tissue graft having a certain shape and/or certain dimensions, and/or to allow culture of such tissue grafts under press-fit direct perfusion conditions. In some embodiments, the perfusion bioreactors comprise an equilibration chamber.

25 Claims, 21 Drawing Sheets

(56) References Cited

U.S. PATENT DOCUMENTS

| | | |
|---|---|---|
| 2008/0033548 A1 | 2/2008 | Xuenong et al. |
| 2010/0249931 A1 | 9/2010 | Laurencin et al. |
| 2010/0303911 A1 | 12/2010 | Sheardown et al. |
| 2011/0151400 A1 | 6/2011 | Boiangiu et al. |
| 2012/0035742 A1 | 2/2012 | Vunjak-Novakovic et al. |
| 2012/0209403 A1 | 8/2012 | Morrison et al. |
| 2013/0017232 A1 | 1/2013 | Varghese |
| 2013/0030547 A1 | 1/2013 | Burkinshaw |
| 2013/0030548 A1 | 1/2013 | Ling |
| 2013/0274892 A1 | 10/2013 | Lelkes et al. |
| 2013/0344114 A1 | 12/2013 | Chang et al. |
| 2014/0030762 A1 | 1/2014 | De Plano et al. |
| 2014/0147419 A1 | 5/2014 | Novakovic et al. |
| 2015/0289889 A1 | 10/2015 | Altschuler et al. |

FOREIGN PATENT DOCUMENTS

| | | |
|---|---|---|
| WO | WO 2006/109137 A1 | 10/2006 |
| WO | WO 2015/103149 A1 | 7/2015 |

OTHER PUBLICATIONS

De Peppo et al.: "*Cultivation of Human Bone-Like Tissue from Pluripotent Stem Cell-Derived Osteogenic Progenitors in Perfusion Bioreactors*"; Methods Mol Biol., Nov. 27, 2013, vol. 1202, pp. 173-184.

Grayson at al.: "*Effects of Initial Seeding Density and Fluid Perfusion Rate on Formation of Tissue-Engineered Bone*"; Tissue Eng Part A, Jul. 11, 2008, vol. 14, pp. 1809-1820.

International Search Report dated Feb. 16, 2016, regarding PCT/US2015/064076.

International Search Report dated Apr. 6, 2015 regarding PCT/US2014/072579.

Chen, F. et al.: "*Anchoring Dental Implant in Tissue-Engineered Bone Using Composite Scaffold A Preliminary Study in Nude Mouse Model* "; Journal of Oral and Maxillofacial Surgery, 2005, 63, 586-591.

International Search Report dated Jun. 22, 2017, regarding PCT/US2017/025390.

Yu, X et al.: "*Bioreactor-based bone tissue engineering: The influence of dynamic flow on osteoblast phenotypic expression and matrix mineralization*" Proceedings of the National Academy of Science, vol. 101 (31); p. 11203-11208.

Extended European Search Report dated Jul. 7, 2017, regarding EP 14 87 7521.6.

Eldesoni, Karam et al.: "High Calcium Bioglass Enhances Differentiation and Survival of Endothelial Progenitor Cells, Inducing Early Vascularization in Critical Size Bone Defects"; PLOS One, Nov. 2013, vol. 8, No. 11, e79058.

Japanese Office Action dated Aug. 23, 2018, regarding JP 2016-543600.

FIG. 5A
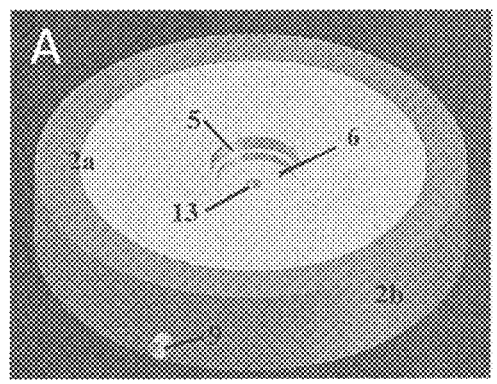
FIG. 5B
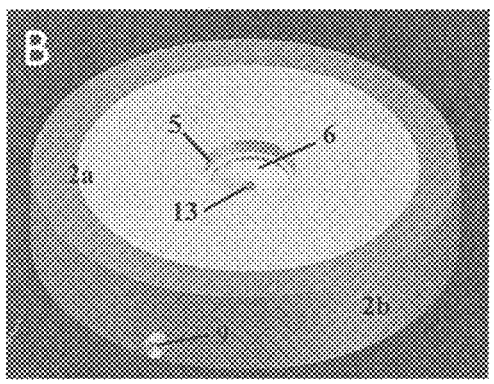
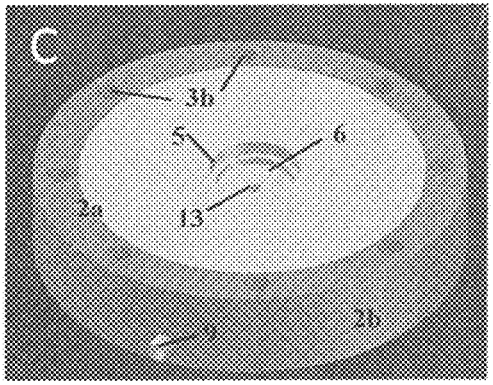
FIG. 5C
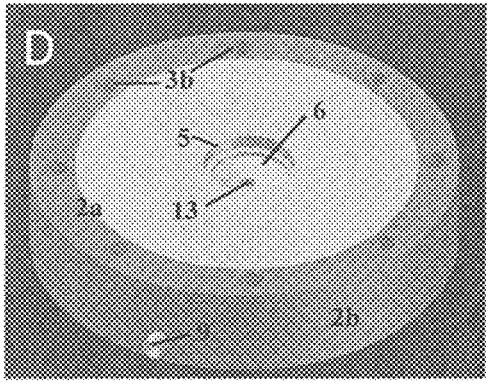
FIG. 5D

PERFUSION BIOREACTOR

CROSS-REFERENCE TO RELATED APPLICATIONS

This application claims the benefit of priority of U.S. Provisional Patent Application No. 62/087,614, filed Dec. 4, 2014, and also claims the benefit of priority of International Patent Application No. PCT/US2014/072579, filed Dec. 29, 2014, which claims the benefit of priority of U.S. Provisional Patent Application No. 62/087,614, filed Dec. 4, 2014, and U.S. Provisional Patent Application No. 61/921,915, filed Dec. 30, 2013, the contents of each of which are hereby incorporated by reference in their entireties.

COPYRIGHT AND INCORPORATION BY REFERENCE

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

BACKGROUND INFORMATION

Field of the Invention

The present invention relates generally to cell culture, and more particularly to a bioreactor and method of use thereof.

Background of the Invention

The human skeleton consists of 206 distinct bones, which support and protect the body, and play a role in metabolism, calcium storage and blood cell production. Despite its ability to remodel throughout a human's lifetime and its self-healing properties, reconstructive therapies are needed to restore functionality in clinical conditions characterized by large skeletal defects resulting from congenital disorders, degenerative diseases and trauma (Braddock, M., Houston, P., et al. Born again bone: tissue engineering for bone repair. *News Physiol Sci* 2001, 16, 208-213). The economic burden of skeletal defects is massive and expected to rapidly increase over the next decades due to the rapid global population growth and extension of life expectancy (Hollinger, J. O., Winn, S., et al. Options for tissue engineering to address challenges of the aging skeleton. *Tissue Eng* 2000, 6, 341-350), with a combined annual US market for bone repair and regeneration therapies projected to reach 3.5 billion by 2017 (U.S. Markets for Orthopedic Biomaterials for Bone Repair and Regeneration. *MedTech Insight* 2013). A large number of bone substitute materials are currently available for skeletal reconstruction, with transplantation of bone grafts still remaining the gold standard treatment (Albert, A., Leemrijse, T., et al. Are bone autografts still necessary in 2006? A three-year retrospective study of bone grafting. *Acta Orthop Belg* 2006, 72, 734-740). Nevertheless, current treatments for patients in need of complex skeletal reconstruction have never reached full clinical potential and can be associated with life-threatening complications. The engineering of viable bone substitutes using a combination of patient-specific cells and compliant biomaterial scaffolds therefore represents a promising therapeutic solution.

Traditional attempts to grow bone grafts in the laboratory were based on culturing cell/scaffold constructs under static conditions in the presence of osteogenesis-inducing factors. However, static cultures are not optimal to grow centimeter-sized bone grafts for clinical translation due to poor nutrient supply and removal of metabolic waste. Under these conditions, in fact, mass transport occurs only via diffusion, which is not sufficient to support cell survival and proliferation inside the core of large cell/scaffold constructs, resulting in necrosis and poor tissue formation. In addition, cell proliferation and matrix synthesis at the construct periphery over the culture period further impede medium diffusion and contribute to the formation of a nutrient gradient that drive cell migration towards the substitute borders (Goldstein, A. S., Juarez, T. M., et al. Effect of convection on osteoblastic cell growth and function in biodegradable polymer foam scaffolds. *Biomaterials* 2001, 22(11), 1279-1288). On top of this, culture in static conditions does not allow provision of those biophysical stimuli that are critical for functional regeneration (Yeatts, A. B., Fisher, J. P. Bone tissue engineering bioreactors: dynamic culture and the influence of shear stress. *Bone* 2011, 48(2), 171-181; Klein-Nulend, J., Bakker, A. D., et al. Mechanosensation and transduction in osteocytes. *Bone* 2013, 54(2), 182-190). Advances in bioreactor systems over the last two decades have opened new opportunities in the field of bone engineering as they allow to nurture the development of bone tissue by providing an appropriate physiological environment with stimulatory biochemical and biophysical signals (Salter, E., Goh, B., et al. Bone tissue engineering bioreactors: a role in the clinic? *Tissue Eng Part B Rev* 2012, 18(1), 62-75).

Bioreactors were initially developed to allow the high-mass culture of cells used for applications in diverse areas, including fermentation, wastewater treatment and purification, food processing and drug production (Martin, I., Wendt, D., et al. The role of bioreactors in tissue engineering. *Trends Biotechnol* 2004, 22(2), 80-86). Many of the principles established by these applications have recently been adapted for tissue engineering purposes. A bioreactor for tissue engineering applications should (i) facilitate uniform cell distribution, (ii) provide and maintain the physiological requirements of the cell (e.g., nutrients, oxygen, growth factors), (iii) increase mass transport both by diffusion and convection using mixing systems of culture medium, (iv) expose cells to physical stimuli, and (v) enable reproducibility, control, monitoring and automation. The ultimate design of a tissue engineering bioreactor is application specific, but basic characteristics are required when engineering tissue substitutes for potential clinical applications, such as the use of materials that do not release toxic products and can withstand numerous cycle of high temperature and pressure for repeated steam sterilization in autoclaves. Furthermore, bioreactors should present a simple design in order to prevent contamination and allow quick access to the engineered tissue if any problem arises in the system during the operational period (e.g. fluid leakage and flow obstruction). Despite the fact that several design solutions and range of stress values imparted to the cells have been explored to date, bioreactors for bone engineering applications are broadly classified in few main categories, including rotating wall vessels, spinner flasks, perfusion bioreactors and compression systems (for review, see Sladkova and de Peppo (2014) Bioreactor systems for human bone tissue engineering, *Processes* 2(2) 494-525.).

Perfusion bioreactors for bone engineering applications are culture systems composed of several key elements, including one or more chambers where the cell/scaffold constructs are placed, a medium reservoir, a tubing circuit and a pump enabling mass transport of nutrients and oxygen throughout the perfusion chamber. Perfusion bioreactors are broadly classified into indirect or direct systems, depending on whether the culture medium is perfused around or throughout the cell/scaffold constructs.

In indirect perfusion bioreactors, the cell/scaffold constructs are loosely placed in the equilibration chamber, and the culture medium preferentially follows the path of least resistance around the constructs, resulting in reduced mass transfer throughout the core of the samples. Therefore, the convective forces generated by the perfusion pump mitigate the nutrient concentration gradients principally at the surface of the cell/scaffold constructs, thus limiting the size of bone substitutes that can be engineered using these systems. On the other hand, indirect perfusion bioreactors may represent valuable systems for the collective culture of a large number of small particulate cell/scaffold constructs that can be then assembled to repair large and geometrically complex skeletal defects (de Peppo, G. M., Sladkova, M., et al. Human embryonic stem cell-derived mesodermal progenitors display substantially increased tissue formation compared to human mesenchymal stem cells under dynamic culture conditions in a packed bed/column bioreactor. *Tissue Eng Part A* 2013, 19, 175-187; David, B., Bonnefont-Rousselot, D., et al. A Perfusion Bioreactor for Engineering Bone Constructs: An in Vitro and in Vivo Study. *Tissue Eng Part C Methods* 2011, 17(5):505-516).

In direct perfusion bioreactors, the cell/scaffold constructs are placed in the equilibration chamber in a press-fit fashion so that the culture medium is forced to pass through the center of the samples. In view of this advantage, direct perfusion bioreactors have been used to engineer bone substitutes using a combination of different human osteocompetent cells and biomaterial scaffolds (for review, see Sladkova and de Peppo (2014) Bioreactor systems for human bone tissue engineering, *Processes* 2(2) 494-525.). Studies demonstrate that direct perfusion of different combinations of cell/scaffold constructs highly support cell survival and proliferation, and formation of mature bone-like tissue, thus representing an optimal culture system for the construction of relevant bone substitutes with potential in clinical application of skeletal reconstructions.

While biomimetic tissue engineering strategies have been explored for ex vivo cultivation of functional bone substitutes by interfacing osteocompetent cells to biomaterials under appropriate culture conditions in bioreactors, engineering large and geometrically complex bone grafts for extensive skeletal reconstructions remains problematic using current engineering approaches. In particular, as discussed above, culture of large bone grafts is problematic using common perfusion bioreactors, due to the flow resistance caused by the large size of the graft. The development of newly formed bone tissue progressively limits the medium perfusion, with negative consequences on the functionality of the perfusion system and graft viability. Thus there remains a need for new approaches and tools to facilitate the in vitro preparation of functional bone tissue and large bone grafts. Such new approaches and tools could also be used for the in vitro preparation of other types of tissue grafts, other than bone.

SUMMARY OF THE INVENTION

Some of the main aspects of the present invention are summarized below. Additional aspects of the present invention are described in the Detailed Description of the Invention, Examples, Drawings and Claims sections of this patent application. The description in each of the sections of this patent application is intended to be read in conjunction with the other sections. Furthermore, the various embodiments described in each of the sections of this patent application can be combined in various different ways, and all such combinations are intended to fall within the scope of the present invention.

To overcome the obstacles of current methods, the present invention provides perfusion bioreactors and cell culture scaffolds for growing functional vascularized tissues, such as bone, in vitro. The size and shape of the scaffolds and bioreactors can be customized using innovative engineering strategies based on a combination of medical imaging, computer-assisted design (CAD) and/or computer-assisted manufacturing (CAM). In addition, digital drawing and simulation software can be used to optimize the design of the perfusion bioreactors, and for driving the controlled manufacturing of the perfusion bioreactors. For example, in some embodiments the present invention provides perfusion bioreactors and cell culture scaffolds to facilitate segmental additive bone engineering (SABE) and/or segmental additive tissue engineering (SATE), which enable segments of functional vascularized tissues, such as bone, to be grown in vitro.

In one embodiment, the invention provides a perfusion bioreactor suitable for use in the preparation of a tissue graft segment, such as a bone graft segment, comprising an equilibration chamber.

In one embodiment, the invention provides a perfusion bioreactor suitable for use in the preparation of a tissue graft segment, comprising at least one graft chamber configured to accommodate a tissue graft segment.

In one embodiment, the invention provides a perfusion bioreactor suitable for use in the preparation of a tissue graft segment, comprising (i) at least one graft chamber and (ii) at least one graft chamber insert configured to accommodate a tissue graft segment.

In one embodiment, the invention provides a perfusion bioreactor suitable for use in the preparation of a tissue graft segment, such as a bone graft segment, comprising: (i) at least one graft chamber configured to accommodate a tissue graft segment; and (ii) at least one equilibration chamber.

In one embodiment, the invention provides a perfusion bioreactor suitable for use in the preparation of a tissue graft segment, comprising (i) at least one graft chamber, (ii) at least one graft chamber insert configured to accommodate a tissue graft segment, and (iii) at least one equilibration chamber.

In one embodiment, the invention provides a perfusion bioreactor suitable for use in preparation of a tissue graft segment, comprising (i) a graft chamber; and (ii) an equilibration chamber in fluid communication with the graft chamber. In one embodiment, the bioreactor further includes an inlet, a fluid channel defining a fluid path between the inlet and the equilibration chamber, a fluid reservoir, and an aperture fluidly connecting the fluid reservoir and the graft chamber, the fluid reservoir further comprising an outlet port.

In one embodiment, the invention provides a perfusion bioreactor suitable for use in the preparation of a tissue graft segment, such as a bone graft segment, comprising: (a) a bottom portion, comprising: (i) at least one graft chamber configured to accommodate a tissue graft segment; (ii) at least one equilibration chamber; (iii) an inlet port; (iv) a fluid channel connecting the equilibration chamber to the inlet port; and (b) a top portion, comprising: (a) a fluid reservoir; (b) at least one opening connecting the fluid reservoir and the graft chamber; and (c) an outlet port. In some such embodiments the top portion and the bottom portion can be secured together using any suitable fastening mechanism.

In some embodiments the perfusion bioreactors described herein may be connected to, or provided together with, a pump, and optionally also one or more tubes to connect the pump to the bioreactor. For example, in one embodiment, the bioreactor may be used in conjunction with, or provided together with, a pump, and one or more tubes connecting the inlet port and/or the outlet port to the pump.

In one embodiment, the invention provides a perfusion bioreactor suitable for use in the preparation of a tissue graft segment, such as a bone graft segment, comprising: (a) a bottom portion, comprising: (i) at least one graft chamber configured to accommodate a tissue graft segment, such as bone graft segment; (ii) at least one equilibration chamber; (iii) an inlet port; (iv) a fluid channel connecting the equilibration chamber to the inlet port; and (b) a top portion, comprising: (a) a fluid reservoir; (b) at least one opening connecting the fluid reservoir and the graft chamber; and (c) an outlet port, wherein the top portion and the bottom portion are secured together by a fastening mechanism; and (c) a pump; and (d) one or more tubes connecting the inlet port, the outlet port and the pump.

In some embodiments, the graft chamber dimensions are designed to accommodate a particular tissue segment, such as a bone segment, for example by using a digital three-dimensional model of the tissue/bone graft segment to custom-design the graft chamber. The graft chamber may have the same size and shape as the tissue/bone segment, or approximately the same size and shape as the tissue/bone segment, or have a size and shape such that the tissue/bone segment will fit into the graft chamber in a press-fit configuration. In some embodiments, the graft chamber further comprises a frame or insert to provide and/or maintain the desired dimensions of the graft chamber (e.g. the desired internal dimensions of the graft chamber, e.g. to accommodate the tissue/bone graft in a press-fit configuration) and/or maintain fluid flow through the perfusion bioreactor. In some embodiments, the frame or insert may be made of or comprise any suitable material. For example, in some embodiments the frame or insert can be made from any material that can easily be molded or cut to have the desired dimensions, such as the dimensions of the tissue/bone graft. In some such embodiments that material may also be compliant, in order to allow the best fit between the graft chamber and the tissue/bone graft. For example, in some embodiments the frame/insert may comprise a biocompatible, non-toxic, moldable plastic, such as silicone or a silicone-like material. In some embodiments, the frame/insert may comprise polydimethylsiloxane (PDMS), e.g. a PDMS ring.

In some embodiments, the tissue/bone graft segment has a maximum thickness of about one centimeter or less. In some embodiments, the tissue/bone graft segment has a maximum thickness of about 0.3 millimeters to about 10 millimeters. In some embodiments, the digital three-dimensional model of the tissue/bone graft segment is generated by medical imaging, computed tomography, computer-assisted design, or any combination thereof.

In some embodiments, the equilibration chamber further comprises a flat floor or a tapered floor. In some embodiments, the equilibration chamber further comprises diffusion frits. In some embodiments, the equilibration chamber further comprises a frame to maintain the dimensions of the equilibration chamber and/or maintain fluid flow through the perfusion bioreactor.

In some embodiments, the fastening mechanism comprises screws, rods, pins, clips, latches or any combination thereof. In some embodiments, the top portion and the bottom portion further comprise one or more holes to facilitate the fastening mechanism. In some embodiments, the bottom portion further comprises a sealing device capable of preventing fluid leakage, for example, one or more o-rings or gaskets. In some embodiments, the bioreactor further comprises a gasket situated between the top portion and bottom portion. In some embodiments, the pump is a peristaltic pump. In some embodiments, the top portion, the bottom portion or both are generated using computer-assisted manufacturing. In some embodiments, the computer-assisted manufacturing comprises three-dimensional printing. In some embodiments the computer-assisted manufacturing comprises a computer-numerical-control milling machine.

In one embodiment, the invention provides a perfusion bioreactor suitable for use in the preparation of a tissue graft segment, such as a bone graft segment, comprising: (a) a bottom portion, comprising: (i) at least one graft chamber configured to accommodate a tissue graft segment, such as a bone graft segment; (ii) at least one equilibration chamber; (iii) an inlet port; (iv) a fluid channel connecting the equilibration chamber to the inlet port; and (b) a top portion, comprising: (a) a fluid reservoir; (b) at least one opening connecting the fluid reservoir and the graft chamber; and (c) an outlet port, wherein the top portion and the bottom portion are secured together by a fastening mechanism; and (c) a pump; and (d) one or more tubes connecting the inlet port, the outlet port and the pump. In some embodiments, the graft chamber dimensions are the same as or similar to a digital three-dimensional model of the tissue/bone graft segment. In some embodiments, the tissue/bone graft segment has a maximum thickness of about one centimeter or less. In some embodiments, the tissue/bone graft segment has a maximum thickness of about 0.3 millimeters to about 10 millimeters. In some embodiments, the digital three-dimensional model of the tissue/bone graft segment is generated by medical imaging, computed tomography, computer-assisted design, or any combination thereof. In some embodiments, the equilibration chamber further comprises a flat floor or a tapered floor. In some embodiments, the equilibration chamber further comprises diffusion frits. In some embodiments, the equilibration chamber further comprises a frame to maintain the dimensions of the equilibration chamber and/or maintain fluid flow through the perfusion bioreactor. In some embodiments, the graft chamber further comprises a frame to maintain the dimensions of the graft chamber and/or maintain fluid flow through the perfusion bioreactor. In some embodiments, a frame may comprise a PDMS ring. In some embodiments, the fastening mechanism comprises screws, rods, pins, clips, latches or any combination thereof. In some embodiments, the top portion and the bottom portion further comprise one or more holes to facilitate the fastening mechanism. In some embodiments, the bottom portion further comprises a sealing device capable of preventing fluid leakage, for example, one or more o-rings or gaskets. In some embodiments, the bioreactor further comprises a gasket situated between the top portion and bottom portion. In some embodiments, the pump is a peristaltic pump. In some embodiments, the top portion, the bottom portion or both are generated using computer-assisted manufacturing. In some embodiments, the computer-assisted manufacturing comprises three-dimensional printing. In some embodiments the computer-assisted manufacturing comprises a computer-numerical-control milling machine.

In one embodiment, the invention provides a cell culture scaffold suitable for use in the preparation of a tissue/bone graft segment, wherein the cell culture scaffold dimensions are the same as or similar to a digital three-dimensional model of the tissue/bone graft segment. In some embodiments, the digital three-dimensional model of the segment of tissue/bone is generated by medical imaging, computed tomography, computer-assisted design, or any combination thereof. In some embodiments, the cell culture scaffold is generated using computer-assisted manufacturing. In some embodiments, the computer-assisted manufacturing comprises three-dimensional printing. In some embodiments, the computer-assisted manufacturing comprises a computer-numerical-control milling machine. In some embodiments, the computer-assisted manufacturing comprises a casting technology. In some embodiments, the manufacturing comprises laser cutting. In some embodiments the manufacturing comprises computer-numerical-control laser cutting. In some embodiments, the cell culture scaffold comprises or consists essentially of decellularized bone tissue, a natural or synthetic ceramic/polymer composite material, a material capable of being absorbed by cells, a biocompatible non-resorbable material, or any combination thereof.

In some embodiments the methods provided by the present invention utilize three-dimensional models of a particular tissue portion (e.g. a portion of tissue to be constructed, replaced, or repaired), in order to make customized tissue culture scaffolds, customized tissue grafts, and/or customized bioreactors for producing such tissue grafts. In some such embodiments the tissue culture scaffolds, tissue grafts, and/or bioreactors are designed and produced such that they have a size and shape corresponding to that of the desired tissue portion, or a segment thereof. In some embodiments the methods of the present invention involve making tissue grafts by producing two or more tissue graft segments that can then be assembled/connected to produce the final tissue graft. Such methods may be referred to herein as segmental additive tissue engineering (SATE) methods. In addition to the various different methods provided herein, the present invention also provides certain compositions and devices, including customized tissue grafts, customized tissue culture scaffolds, customized bioreactors, customized bioreactor graft chambers, and customized bioreactor graft chamber inserts. These and other aspects of the present invention are described in more detail below and throughout the present patent specification.

In some embodiments, the present invention provides a method of preparing a tissue graft, comprising: (a) obtaining a three-dimensional model of a tissue portion to be produced, replaced, or repaired, (b) partitioning the three-dimensional model into two or more model segments, (c) preparing two or more tissue graft segments, wherein each tissue graft segment has a size and shape corresponding to one of the model segments of step (b), and (d) assembling the two or more tissue graft segments to form a tissue graft.

In embodiments, preparing a tissue graft segment comprises: (i) obtaining a scaffold, wherein the scaffold has a size and shape corresponding to a segment of a tissue portion to be produced, replaced, or repaired (a tissue segment) or a three dimensional model thereof (a model segment), (ii) applying one or more populations of cells to the scaffold, and (iii) culturing the cells on the scaffold using a perfusion bioreactor of the present invention to form a tissue graft segment.

In some embodiments the present invention provides a method of preparing a tissue graft segment (for example for use in conjunction with one of the methods described above or elsewhere herein), wherein the method comprises: (i) obtaining a scaffold, wherein the scaffold has a size and shape corresponding to a segment of a tissue portion to be produced, replaced, or repaired (a tissue segment) or a three dimensional model thereof (a model segment), (ii) applying one or more populations of cells to the scaffold, (iii) obtaining a perfusion bioreactor comprising a graft chamber configured to accommodate the scaffold, (for example having a graft chamber or graft chamber insert having an internal size and shape corresponding to the scaffold), (iv) inserting the scaffold into the graft chamber of the culture vessel, and (v) culturing the cells on the scaffold within the bioreactor to form a tissue graft segment.

In some embodiments the present invention provides a method of preparing a tissue graft segment (for example for use in conjunction with one of the methods described above or elsewhere herein), wherein the method comprises: (i) obtaining a scaffold, wherein the scaffold has a size and shape corresponding to a segment of a tissue portion to be produced, replaced, or repaired (a tissue segment) or a three dimensional model thereof (a model segment), (ii) obtaining a bioreactor comprising a graft chamber configured to accommodate the scaffold, (for example having a graft chamber or graft chamber insert having an internal size and shape corresponding to the scaffold), (iii) inserting the scaffold into the graft chamber of the culture vessel, (iv) applying one or more populations of cells to the scaffold in the graft chamber, and (v) culturing the cells on the scaffold within the bioreactor to form a tissue graft segment.

In some embodiments, the present invention provides various methods of preparing bioreactors, bioreactor graft chambers, or bioreactor graft chamber inserts, suitable for use in preparing the tissue grafts and/or tissue graft segments described herein.

In one such embodiment, the present invention provides a method of preparing a bioreactor, bioreactor graft chamber, or bioreactor graft chamber insert, comprising: obtaining a three-dimensional model of a tissue portion to be produced, replaced, or repaired.

In another such embodiment, the present invention provides a method of preparing a bioreactor of the present invention, comprising: (a) obtaining a three-dimensional model of a tissue portion to be produced, replaced, or repaired, and (b) partitioning the three-dimensional model into two or more segments (model segments).

In another such embodiment, the present invention provides a method of preparing a bioreactor of the present invention, comprising: obtaining a three-dimensional model of a tissue portion to be produced, replaced, or repaired wherein the model has been partitioned into two or more segments (model segments).

In another such embodiment, the present invention provides a method of preparing a bioreactor of the present invention, comprising: (a) obtaining a three-dimensional model of a tissue portion to be produced, replaced, or repaired, (b) partitioning the three-dimensional model into two or more model segments, (c) preparing two or more bioreactors, wherein each has an internal size and shape that corresponds to the size and shape of one of the model segments of (b).

In addition to the methods described above, numerous variations on such embodiments are envisioned and are within the scope of the present invention, including, but not limited to embodiments that combine any one or more of the methods or method steps described above, or alter the order of any of the method steps described above.

In some embodiments, the present invention provides tissue grafts, and segments thereof (tissue graft segments). For example, in some embodiments, the present invention provides tissue grafts and tissue graft segments made using any of the methods described herein.

In one embodiment the present invention provides a tissue graft comprising two or more tissue graft segments. In one embodiment the present invention provides a tissue graft comprising two or more tissue graft segments, wherein the tissue graft has a shape and size corresponding to a tissue portion to be replaced or repaired, or a three-dimensional model thereof.

In one embodiment the present invention provides a tissue graft comprising two or more tissue graft segments, wherein each tissue graft segment has a maximum thickness (i.e. at its thickest point) of from about 0.3 millimeters to about 10 millimeters.

In one embodiment the present invention provides a tissue graft comprising two or more tissue graft segments, wherein each tissue graft segment comprises tissue cells differentiated from stem cells or progenitor cells (e.g. induced pluripotent stem cells).

In one embodiment the present invention provides a tissue graft comprising two or more tissue graft segments, wherein each tissue graft segment comprises endothelial cells, such as endothelial cells differentiated from stem cells or progenitor cells (e.g. induced pluripotent stem cells).

In one embodiment the present invention provides a vascularized tissue graft comprising two or more tissue graft segments, wherein each tissue graft segment has a maximum thickness (i.e. at its thickest point) of from about 0.3 millimeters to about 10 millimeters.

In one embodiment the present invention provides a vascularized bone graft comprising two or more bone graft segments, wherein each bone graft segment has a maximum thickness (i.e. at its thickest point) of from about 0.3 millimeters to about 10 millimeters and wherein the bone graft comprises bone cells derived from stem cells or progenitor cells (e.g. induced pluripotent stem cells) and endothelial cells derived stem cells or progenitor cells (e.g. induced pluripotent stem cells).

In addition to the tissue grafts described above, numerous variations of such tissue grafts are envisioned and are within the scope of the present invention, including, but not limited to those described elsewhere in the present specification and those that combine any one or more of the elements described above or elsewhere in the application.

In some embodiments, the present invention provides bioreactors of the present invention. For example, in some embodiments, the present invention provides bioreactors made using any of the methods described herein.

In one embodiment the present invention provides bioreactors of the present invention, wherein the internal portion thereof has a size and shape corresponding to the tissue portion to be replaced or repaired, a segment of the tissue portion to be replaced or repaired, or a three-dimensional model of any thereof.

In one embodiment the present invention provides bioreactors of the present invention, wherein the internal portion thereof is designed to accommodate a scaffold or a tissue graft segment that has a size and shape corresponding to a segment of a tissue portion to be replaced or repaired.

In one embodiment the present invention provides bioreactors of the present invention, wherein the internal portion thereof is designed to accommodate a scaffold or a tissue graft segment, wherein each tissue graft segment has a maximum thickness (i.e. at its thickest point) of from about 0.3 millimeters to about 10 millimeters.

In addition to the bioreactors described herein, numerous variations of such bioreactors, bioreactor graft chambers, and bioreactor graft chamber inserts are envisioned and are within the scope of the present invention, including, but not limited to, those described elsewhere in the present specification and those that combine any one or more of the elements described above or elsewhere in the application.

In some of the above embodiments, the tissue grafts or tissue graft segments are bone tissue grafts or bone tissue graft segments. In some embodiments, the tissue grafts or tissue graft segments are cartilage grafts or cartilage graft segments.

In some of the above embodiments, the tissue grafts or tissue graft segments comprise mammalian cells, such as cells from non-human primates, sheep, or rodents (such as rats or mice). In some of the above embodiments, the tissue grafts or tissue graft segments comprise human cells. In some of the above embodiments, the tissue grafts or tissue graft segments comprise one or more populations of cells derived from the same subject into which the tissue graft is to be implanted (i.e. autologous cells). In some of the above embodiments, the tissue grafts or tissue graft segments comprise one or more populations of cells derived from stem cells or progenitor cells, such as induced pluripotent stem cells.

In some of the above embodiments, the tissue grafts or tissue graft segments are vascularized. In some of the above embodiments, the tissue grafts or tissue graft segments comprise endothelial cells, such as endothelial cells derived from stem cells or progenitor cells, such as induced pluripotent stem cells.

In some of the above embodiments the three-dimensional models and/or model segments are digital models, such as digital models that provide a representation of the three-dimensional structure of a tissue portion or a segment thereof.

In some of the above embodiments the tissue graft segments have a thickness of about 20 millimeters or less, or 15 millimeters or less, or 10 millimeters or less, for example at their thickest point. For example, in some of the above embodiments the tissue graft segments have a thickness of from about 0.3 millimeters to about 10 millimeters, for example at their thickest point.

In some of the above embodiments the culture vessels are bioreactors, such as direct perfusion bioreactors. In some of the above embodiments the scaffolds or tissue graft segments are placed into bioreactors under press-fit conditions. In some of the above embodiments tissue graft segments are cultured in a bioreactor or the present invention under direct perfusion and/or press-fit conditions.

In some of the above embodiments the scaffolds are generated or customized using computer assisted manufacturing, three-dimensional printing, casting, milling, laser cutting, rapid prototyping, or any combination thereof.

In some of the above embodiments the bioreactors are generated or customized using computer assisted manufacturing, three-dimensional printing, casting, milling, laser cutting, rapid prototyping, or any combination thereof.

In some of the above embodiments, the tissue grafts comprise two or more tissue graft segments connected using a biocompatible adhesive, stitches, sutures, staples, plates, pins, screws, or any combination thereof.

In some embodiments the methods, compositions, and devices provided by the present invention, and tissues prepared therefrom, can be useful for a variety of applications including for therapeutic purposes (such as repairing pathological or traumatic tissue defects), cosmetic purposes, or in model systems for studying diseases or developing therapeutics.

BRIEF DESCRIPTION OF THE FIGURES

FIG. 1A: Customized perfusion bioreactors secured using side latches. FIG. 1B: Customized perfusion bioreactors secured using screws.

FIG. 2A: Top view of the customized bioreactor of FIG. 1A. FIG. 2B: Bottom view of the customized bioreactor of FIG. 1B.

FIG. 4A: Gasket used to seal the perfusion bioreactor of FIG. 1A secured with side latches. FIG. 4B: Gasket used to seal the perfusion bioreactor of FIG. 1B secured with screws.

FIGS. 5A-5D. Top side views of the bottom portion of customized perfusion bioreactors showing the graft chamber 5, the equilibration chamber 6 and perfusion channel 7 (between opening 13 and inlet port 9). FIG. 5A: Flat equilibration chamber for latch-secured perfusion bioreactors. FIG. 5B: Tapered equilibration chamber for latch-secured perfusion bioreactors. FIG. 5C: Flat equilibration chamber for screw-secured perfusion bioreactors. FIG. 5D: Tapered equilibration chamber for screw-secured perfusion bioreactors.

FIG. 6A: Flat equilibration chamber for latch-secured perfusion bioreactors. FIG. 6B: Tapered equilibration chamber for latch-secured perfusion bioreactors. FIG. 6C: Flat equilibration chamber for screw-secured perfusion bioreactors. FIG. 6D: Tapered equilibration chamber for screw-secured perfusion bioreactors.

FIG. 7A: Flat equilibration chamber for latch-secured perfusion bioreactors. FIG. 7B: Tapered equilibration chamber for latch-secured perfusion bioreactors. FIG. 7C: Flat equilibration chamber for screw-secured perfusion bioreactors. FIG. 7D: Tapered equilibration chamber for screw-secured perfusion bioreactors.

FIG. 8A: Flat equilibration chamber 6. FIG. 8B: Tapered equilibration chamber 6.

FIG. 9A: Flat equilibration chamber 6. FIG. 6B: Tapered equilibration chamber 6.

FIG. 6B: Flat equilibration chamber 6 for screw-secured perfusion bioreactors.

FIGS. 12A-12B. Perspective view of exemplary cell culture scaffolds provided by the invention. FIG. 12A: Shows an enlarged view of a single scaffold. The scaffold can be designed and manufactured based on a digital image of a portion of tissue, as described herein. FIG. 12B: Shows multiple scaffolds of different shapes and sizes. Multiple scaffolds can be used, for example, to prepare complementary segments of a large bone graft, as described herein.

FIG. 13A: Perspective view of the bottom portion of an exemplary multi-chamber perfusion bioreactor for the collective culture of more than one bone segment. FIG. 13B: Perspective view of the top portion of an exemplary multi-chamber perfusion bioreactor for the collective culture of more than one bone segment.

FIG. 15A: Three-dimensional digital model of a human femur with a digital reconstruction of a bone defect to be repaired (dark gray). FIG. 15B: Partitioning of the digital model of the bone defect shown in FIG. 15A into five model segments (dark gray). The model segments can be used to drive the manufacturing of biomaterial scaffolds (light gray) having a size and shape that corresponds to each of the model segments.

DETAILED DESCRIPTION OF THE INVENTION

Figure 1A:
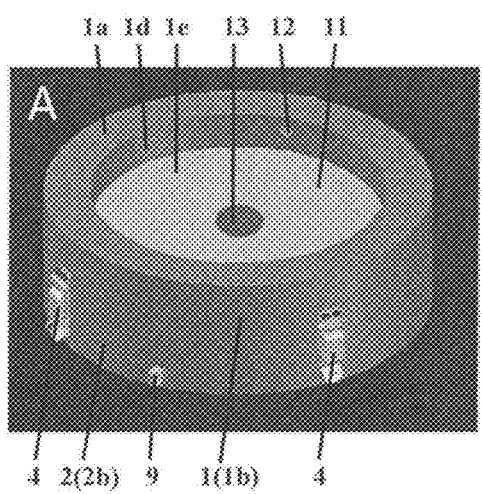
FIGS. 1A-1B. Top side view of two embodiments of the customized perfusion bioreactors.

In some embodiments the present invention provides novel perfusion bioreactors and cell scaffolds that may facilitate the engineering of large and/or geometrically defined tissue/bone grafts. In some embodiments the size and shape of the bioreactors and scaffolds may be based on digital models of a tissue to be repaired, e.g. a bone defect. In some embodiments the digital model of the tissue defect may be partitioned in sequential segments using computer-aided design (CAD) software, then the models of the tissue segments may be used as a reference for the computer-aided manufacture (CAM) of custom-made perfusion bioreactors and production of scaffolds of corresponding size and shape. In some embodiments bioreactors may accommodate each specific cell/scaffold construct in a press-fit fashion and allow culture under direct perfusion conditions.

In embodiments, perfusion bioreactors provided by the invention comprise a bottom portion and a top portion. It will be appreciated that the bottom portion and top portion may be a single unitary form, i.e., a single piece, such that leakage is prevented between the bottom and top portions. In some embodiments, the bottom portion comprises one or more graft chamber(s) (configured to accommodate one or more bone graft segment(s)), one or more equilibration chambers, a fluid inlet port, and one or more fluid channels connecting the equilibration chamber(s) to the fluid inlet port. The equilibration chamber will typically be positioned beneath the graft chamber so as to ensure homogenous perfusion and support the graft. In some embodiments, the top portion comprises a fluid reservoir (e.g., for cell culture medium), one or more openings (to connect the fluid reservoir (of the top portion) and the graft chamber(s) (of the bottom portion)), and a fluid outlet port. In some embodiments, the top portion and the bottom portion are secured together by a fastening mechanism (such as, for example, latches or screws). In some embodiments, the bioreactors further comprise a pump, for example a peristaltic pump, and one or more tubes connecting the inlet and outlet ports to facilitate fluid flow through the bioreactor. In some embodiments, the bioreactors comprise one or more gaskets or o-rings or other structures capable of sealing the bioreactor and/or preventing fluid leakage or spillage. In some embodiments, one or more diffusion enhancing elements, such as diffusion frits, can be placed into the equilibration chamber to improve fluid flow and homogenous graft perfusion. In some embodiments, frames or inserts, for example PDMS frames or inserts, can be placed or inserted into the graft chamber and/or the equilibration chamber to secure the graft in place and enable culture of the tissue segment under direct perfusion, as well as to modulate the shape and dimensions of the graft chamber and equilibration chamber.

The customized design and manufacture of the bioreactors, and each element or structure of the bioreactors is described in further detail herein.

Some of the main embodiments of the present invention are described in the above Summary of the Invention section of this application, as well as in the Examples, Figures and Claims. This Detailed Description of the Invention section provides additional description relating to the compositions and methods of the present invention, and is intended to be read in conjunction with all other sections of the present patent application, including the Summary of the Invention, Examples, Figures and Claims sections of the present application.

Abbreviations & Definitions

The abbreviation "CAD" refers to computer-aided design.

The abbreviation "CAM" refers to computer-aided manufacture.

The abbreviation "CNC" refers to computer-numerical-control.

As used herein, the terms "cell/scaffold" and "scaffold/cell" and "cell/scaffold construct" and "cell/scaffold complex" and "scaffold/cell construct" and "scaffold/cell complex" are used interchangeably to refer to a scaffold to which cells have been applied.

As used herein, the terms "about" and "approximately," when used in relation to numerical values, mean within + or −20% of the stated value.

Additional definitions and abbreviations are provided elsewhere in this patent specification or are well known in the art.

FIGS. 1 through 13 show exemplary bioreactors and scaffolds according to the invention. While the designs shown in the Figures are illustrative of the various different features of the bioreactors and scaffolds of the invention, the invention is not limited to the specific designs provided in the drawings. Rather, variations and modifications of the designs shown in the Figures are contemplated and are within the scope of the present invention, as described herein and as would be understood by those of ordinary skill in the art.

Figure 1B:
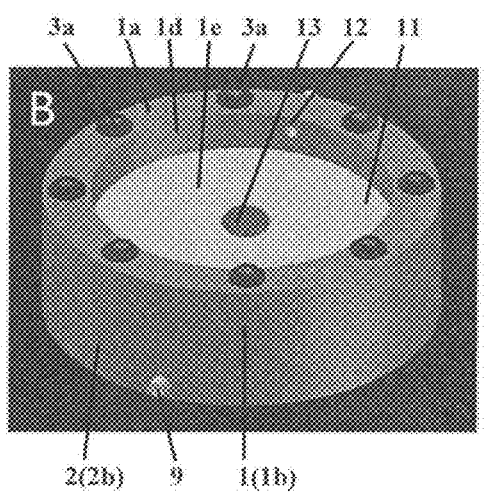

FIG. 1 is a perspective view of exemplary bioreactors with illustrative fastening mechanisms securing the top portion 1 to the bottom portion 2 of the bioreactor—FIG. 1A shows latches 4 as the fastening mechanism. In this embodiment, the latches 4 are positioned on the exterior side surface of the top portion 1b and the exterior side surface of the bottom portion 2b. FIG. 1B shows screws 3a as the fastening mechanism. In this embodiment, the screws are inserted into holes in the top surface of the top portion 1a and fasten into appropriately placed holes in the top surface of the bottom element (see FIGS. 5C and 5D). Further illustrated in both FIGS. 1A and 1B is an outlet port 12 in the top portion of the bioreactor, and an inlet port 9 in the bottom portion. The outlet port 12 is illustrated here as an opening or channel through the side surface 1b of the top portion that allows fluid (e.g., cell culture medium) to exit the fluid reservoir 11, flow through a tube or tubes (see FIG. 11), then through a perfusion channel (see FIG. 2B) to the inlet port 9, an opening or channel through the side surface 2b in the bottom portion of the bioreactor which allow the flow of fluids through the bioreactor. The fluid reservoir 11 is a chamber in the top portion formed by the interior side surface 1d and interior bottom surface 1e of the top portion. Fluid, for example, cell culture medium may be transferred to or from the fluid reservoir using pipets or the like.

Figure 2A:
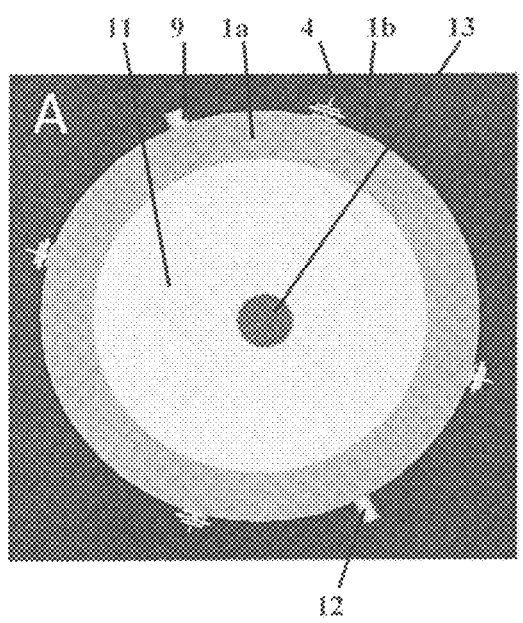
FIGS. 2A-2B.
Figure 2B:
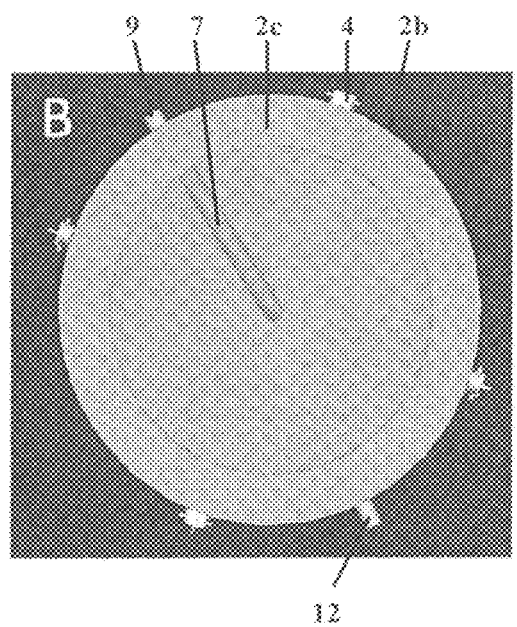

FIG. 2 is a top view (FIG. 2A) and bottom view (FIG. 2B) of an assembled bioreactor. FIG. 2A shows the top surface 1a of the top portion of the bioreactor and latches 4 on the side surface 1b, a fluid reservoir 11 with an opening (perfusion exit) 13, and an outlet port 12. The inlet port 9 of the bottom portion is also visible in FIG. 2A. FIG. 2B shows the bottom surface 2c of the bottom portion of the bioreactor and latches 4 on the side surface 2b, an internal perfusion channel 7 is illustrated that connects to the inlet port 9. The outlet port 12 of the top portion is also visible in FIG. 2B.

Figure 3A:
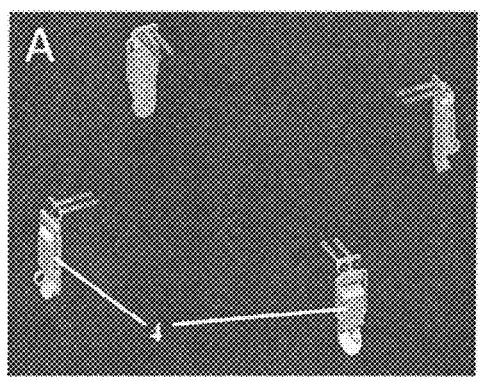
FIGS. 3A-3B. Top side view of the latches (A) and screws (B) used to secure the customized perfusion bioreactors of FIGS. 1A and 1B.
Figure 3B:
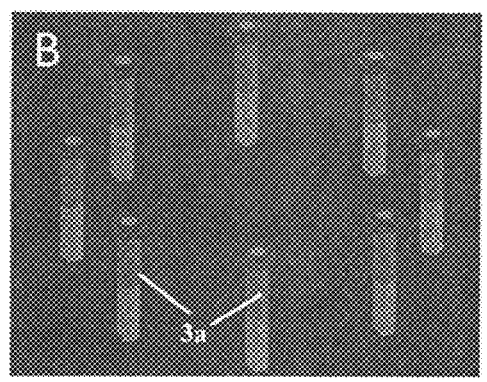

FIG. 3 shows a perspective view of exemplary arrangements illustrative fastening mechanisms, latches 4 (FIG. 3A) and screws 3a (FIG. 3B).

Figures 4A, 4B:
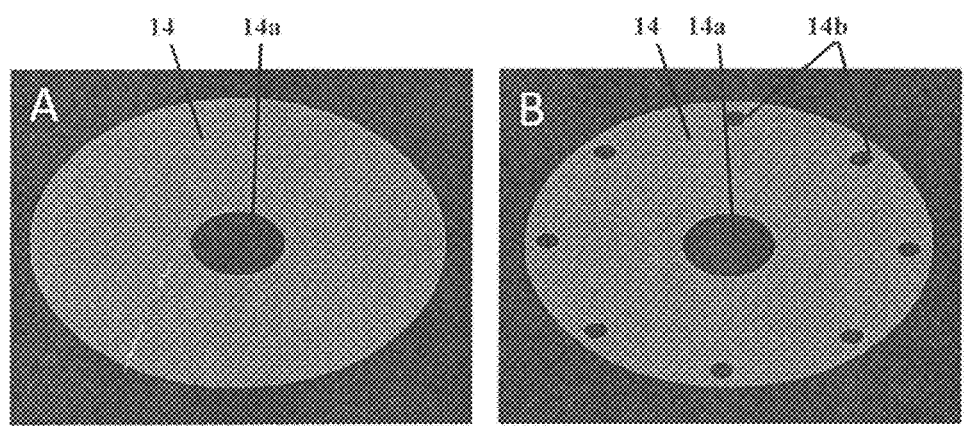
FIGS. 4A-4B. Top side view of the gaskets used to seal the junction between bottom and top portions of the customized bioreactors of FIGS. 1A and 1B.
Figure 6A:
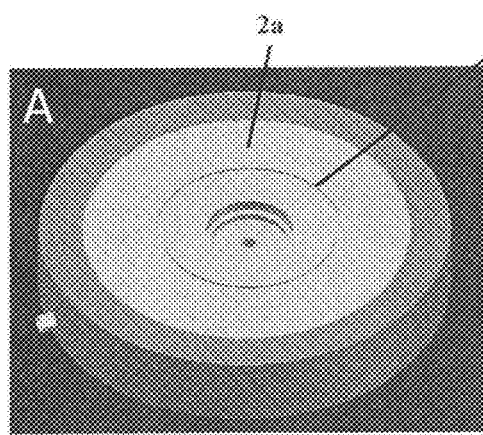
FIGS. 6A-6D. Top side views of the bottom portion of the customized perfusion bioreactors showing a circular groove 8 surrounding the graft chamber 5 used to accommodate an O-ring preventing medium leakage.
Figure 6B:
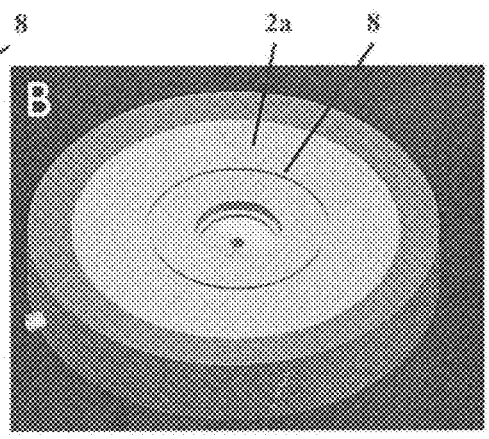
Figure 6C:
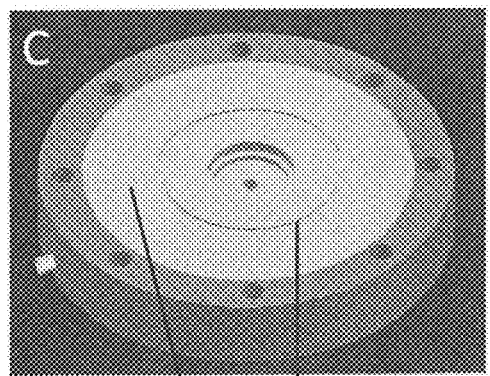
Figure 6D:
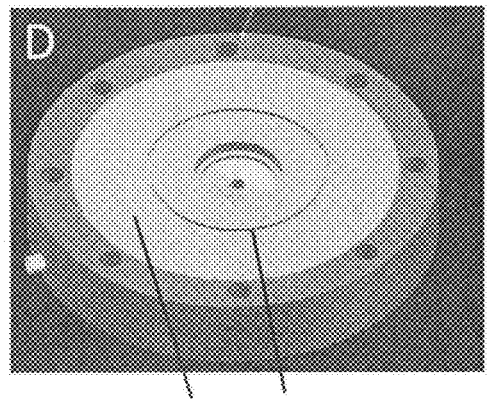
Figure 7A:
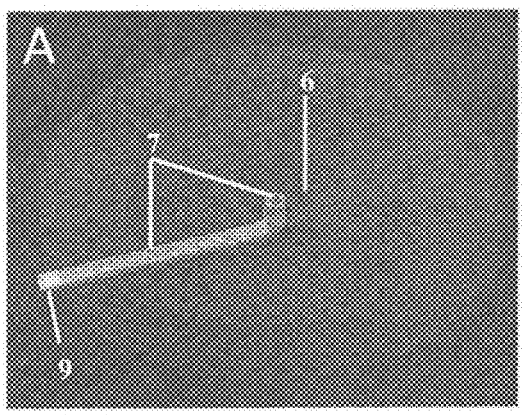
FIGS. 7A-7D. Top side views of the bottom portion of the customized perfusion bioreactors showing the inlet port 9 and perfusion channel 7.
Figure 7B:
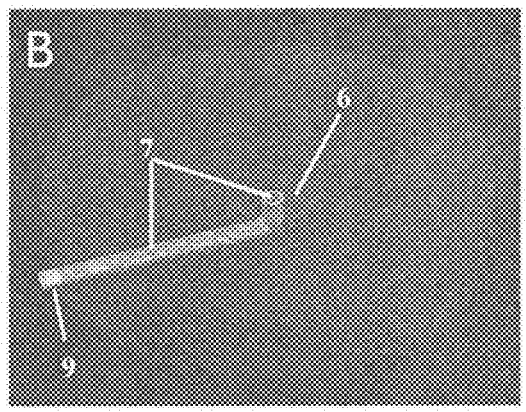
Figure 7C:
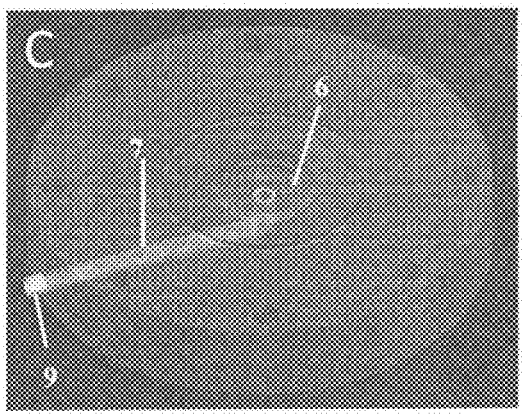
Figure 7D:
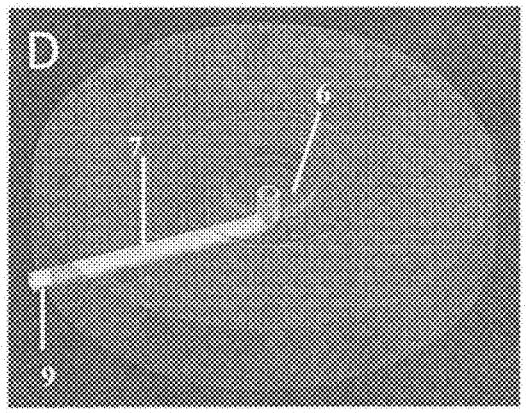

FIG. 4 shows an exemplary gasket to seal the junction between the top and bottom portions of a bioreactor. The gasket 14 comprises an opening 14a to accommodate the complementary openings and chambers in the top and bottom portions of the bioreactor. FIG. 4A shows a gasket suitable for a bioreactor secured by latches. The gasket shown in FIG. 4B comprises holes 14b to accommodate a bioreactor secured by screws.

FIG. 5 shows an illustrative embodiment of the bottom portion of a perfusion bioreactor. FIGS. 5A and 5C each show an exemplary equilibration chamber 6 having a flat floor/bottom surface. FIGS. 5B and 5D each show an exemplary equilibration chamber 6 having a tapered floor/bottom surface. In some embodiments, the floor of the equilibration chamber may have any suitable shape, including but not limited to, straight, curved, beveled, chamfered, or any other suitable shape, as desired. The bottom portion in FIGS. 5A and 5D are suitable for fastening by latches. The bottom portions in FIGS. 5C and 5D comprise holes 3b to accommodate fastening by screws. Further elements shown in FIGS. 5A-5D include the top surface 2a and side surface 2b of the bottom portion, a graft chamber 5, an opening (perfusion exit) 13, and an inlet port 9.

FIGS. 6A-6D show a further embodiment of the bottom portions shown in FIG. 5A-5D, respectively, where an o-ring groove 8 is illustrated on the top surface 2a of the bottom portion.

FIGS. 7A-7D show a transparent view of the bottom portions shown in FIGS. 5A-5D, respectively, where the perfusion channel 7 is visible on the interior of the bottom portion. The perfusion channel facilitates fluid flow between the inlet port 9 and the equilibration chamber 6.

Figures 8A, 8B:
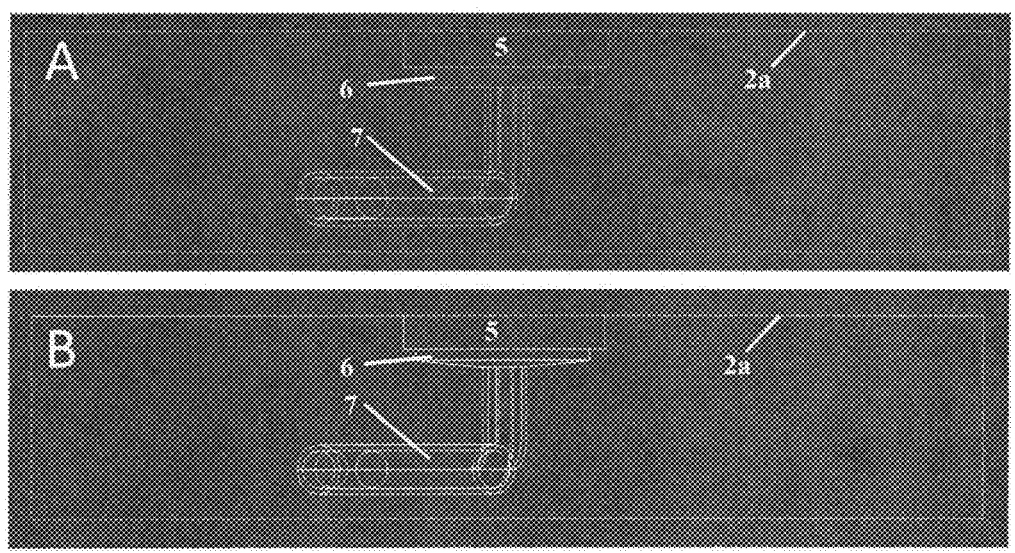
FIGS. 8A-8B. Cross sectional views of the bottom portion of the customized perfusion bioreactors showing the equilibration chamber 6, the graft chamber 5 and perfusion channel 7.

FIG. 8 shows a cross-section view of an exemplary bottom portion of a bioreactor having a flat equilibration chamber 6 (FIG. 8A) or a tapered equilibration chamber 6 (FIG. 8B). Further elements shown in FIGS. 8A and 8B include the top surface 2a of the bottom portion, a graft chamber 5, and a perfusion channel 7.

Figure 9A:
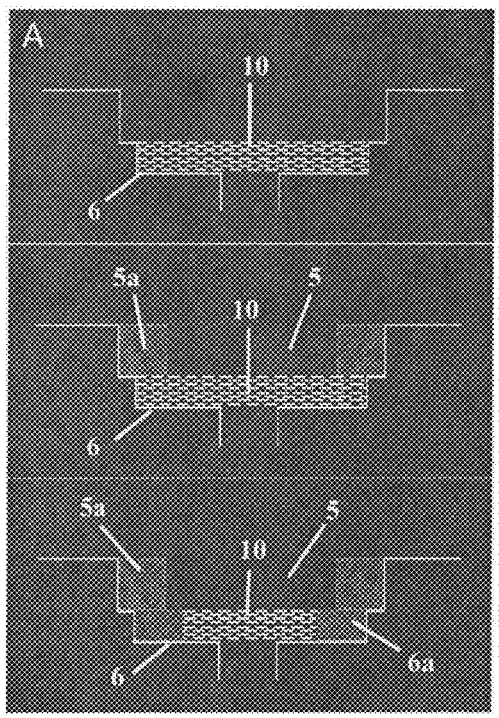
FIGS. 9A-9B. Schematic cross sectional views of the graft chamber 5 and equilibration chamber 6 of the customized bioreactors showing optional elements including diffusion fits 10, graft chamber frame 5a, and the equilibration chamber frame 6a used to firmly secure the graft in place and enable direct perfusion, and modulate the dimensions of the graft and equilibration chambers.
Figure 9B:
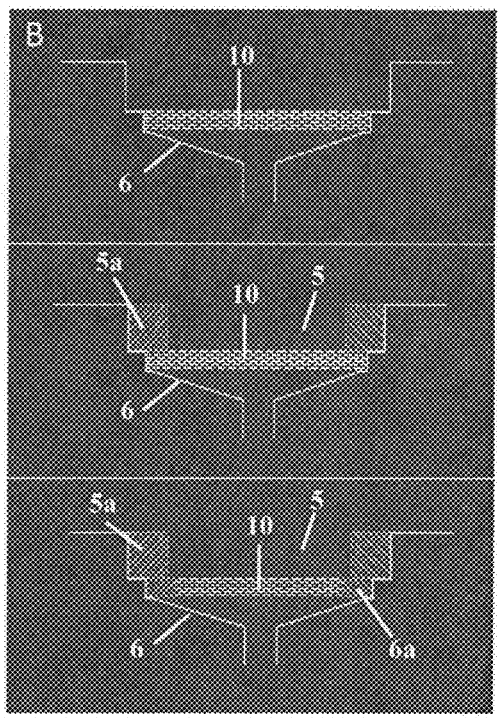

FIG. 9 shows a cross section view of exemplary graft chamber 5 and equilibration chambers 6 in the bottom portion of a bioreactor. The top, middle, and bottom panels of FIG. 9A illustrate embodiments of prefusion chambers 6 having a flat floor. The top, middle, and bottom panels of FIG. 9B illustrate embodiments of equilibration chambers 6 having a tapered floor. In the embodiments shown in the top panels of FIGS. 9A and 9B, diffusion frits 10 are located within the equilibration chamber. Diffusion frits can be used within the context of the invention, for example, to redirect and/or redistribute fluid in the prefusion chamber of the bioreactor to allow for optimal perfusion of the bone segment. In the embodiments shown in the middle panels of FIGS. 9A and 9B, exemplary diffusion frits 10 are present in the equilibration chamber and a graft frame 5a is shown within the graft chamber 5. In the embodiments shown in the bottom panels of FIGS. 9A and 9B, diffusion frits 10 are present in the equilibration chamber and an exemplary graft frame 5a is present in the graft chamber 5, also shown is an exemplary perfusion frame 6a within the equilibration chamber 6. The graft frame and/or perfusion frame are used to firmly secure the growing bone segment in place (press-fit) to enable direct fluid perfusion through the bone segment, and to modulate the dimensions of the graft chamber and equilibration chamber as desired to accommodate the size and shape of the bone segment. The frames may be made of any suitable material including plastic, such as biocompatible plastic, or silicone, such as polydimethylsiloxane (PDMS).

Figures 10A, 10B:
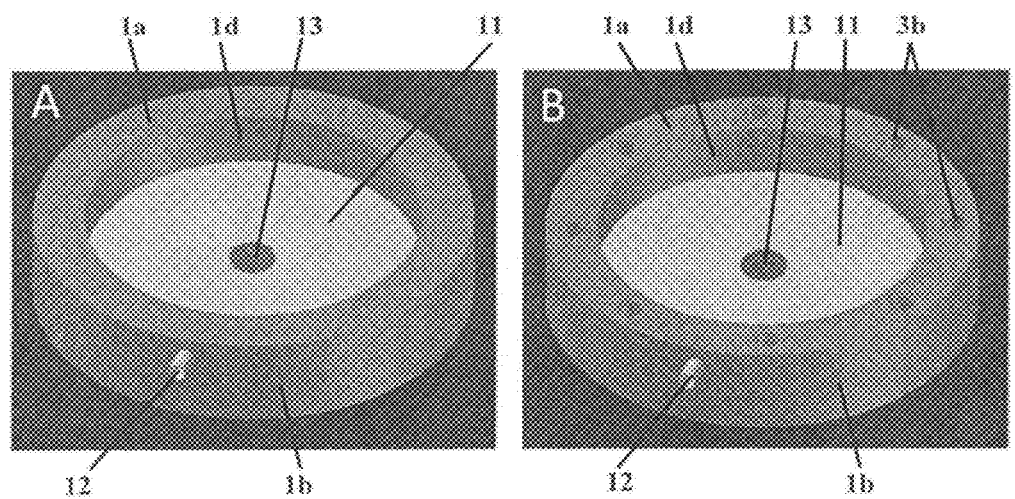
FIGS. 10A-10B. Top side views of the top portion of the customized perfusion bioreactors showing the perfusion exit 13, the fluid reservoir 11 and outlet port 12.

FIG. 10 is a perspective view of exemplary top portions of a bioreactor. FIGS. 10A and 10B illustrate the top surface 1a, exterior side surface 1b, and interior side surface 1d of the top portion, a fluid reservoir 11 comprising an opening 13 (perfusion exit), and an outlet port 12. The top portion shown in FIG. 10A is suitable for fastening by latches. The top portion in FIG. 10B comprises holes 3b to accommodate fastening by screws.

Figure 11:
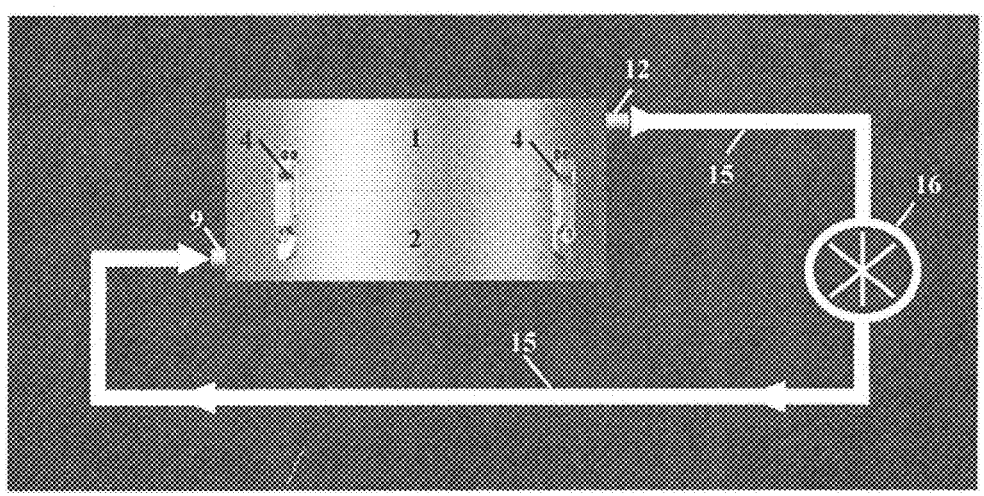
FIG. 11. Side view of the customized perfusion bioreactor showing the system of tubes 15 and peristaltic pump 16 controlling medium perfusion.

FIG. 11 is a side view of an exemplary perfusion bioreactor where the top portion 1 is fastened to the bottom portion 2 with latches 4. One or more tubes 15 can be used to connect the outlet port 12 in the top portion to the inlet port 9 in the bottom portion. A pump 16, such as a peristaltic pump, can be used to control the flow of fluid through the bioreactor.

Figure 12A:
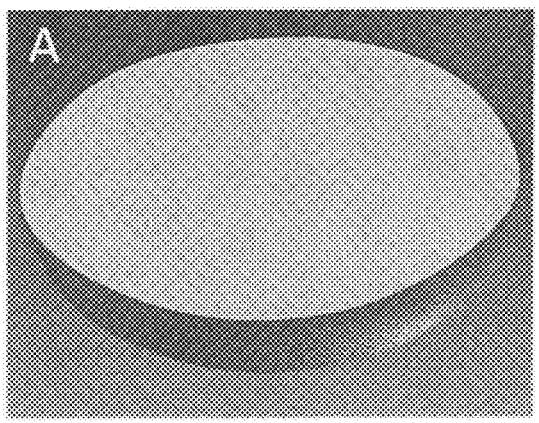
FIG. 12A: Flat equilibration chamber 6 for latch-secured perfusion bioreactors.
Figure 12B:
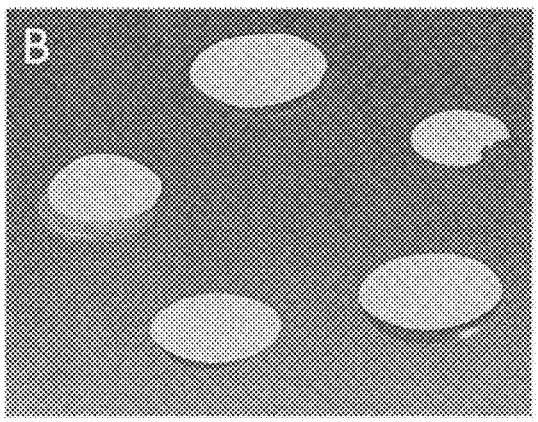

FIG. 12 is a perspective view of exemplary cell culture scaffolds provided by the invention. FIG. 12A shows an enlarged view of a single scaffold. The scaffold can be designed and manufactured based on a digital image of a bone graft segment, as described herein. FIG. 12B shows multiple scaffolds of different shapes and sizes. Multiple scaffolds can be used, for example, to prepare complementary segments of a large bone graft, as described herein.

Figure 13A:
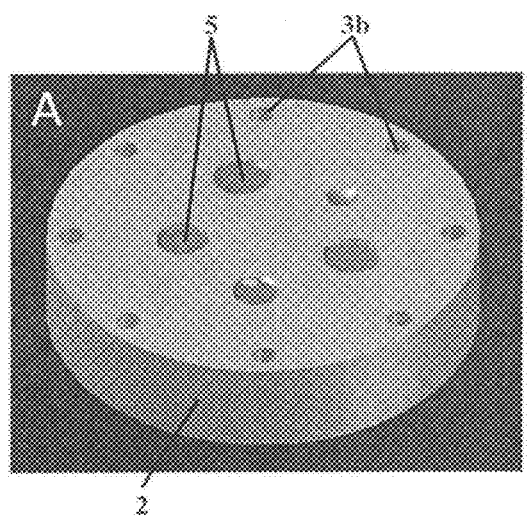
FIGS. 13A-13B.
Figure 13B:
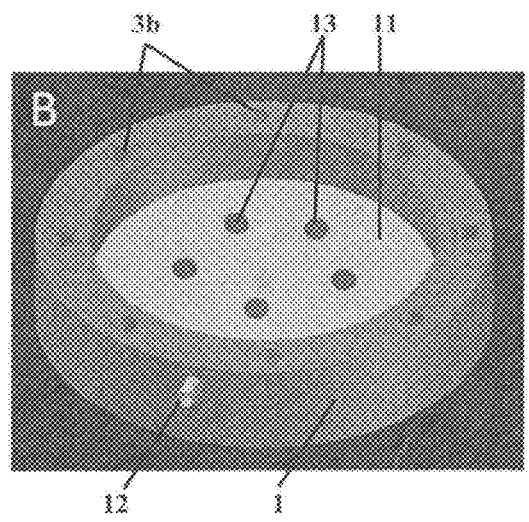

FIG. 13 is a perspective view of the top portion (FIG. 13A) and bottom portion (FIG. 13B) of an exemplary multi-chamber bioreactor provided by the invention. FIG. 13A: The bottom portion 2 comprises multiple graft chambers 5 for the collective culture of bone segments. The graft chambers are shown in various sizes and shapes as desired to accommodate the sizes and shapes of the bone segments. Also shown are holes 3b to facilitate fastening by screws. FIG. 13B: The top portion 1 comprises a fluid reservoir 11, an outlet port 12, and multiple openings 13 aligned with the graft chambers in the bottom portion so as to connect the fluid reservoir to the graft chambers in the bottom portion (FIG. 13A). Also shown are holes 3b to facilitate fastening by screws.

Figure 16:
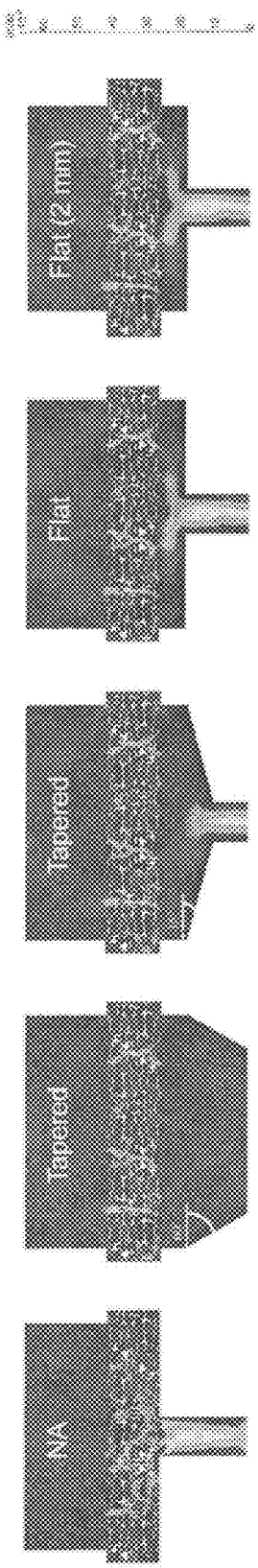
FIG. 16. Simulation studies highlighting the need for an equilibration chamber, and revealing the effect of its geometry on medium perfusion throughout the tissue graft. Studies were performed in Comsol Multiphysics and were essential to guide bioreactor design. Depicted are equilibration chambers have a flat bottom and equilibration chambers having a tapered bottom.
Figure 17:
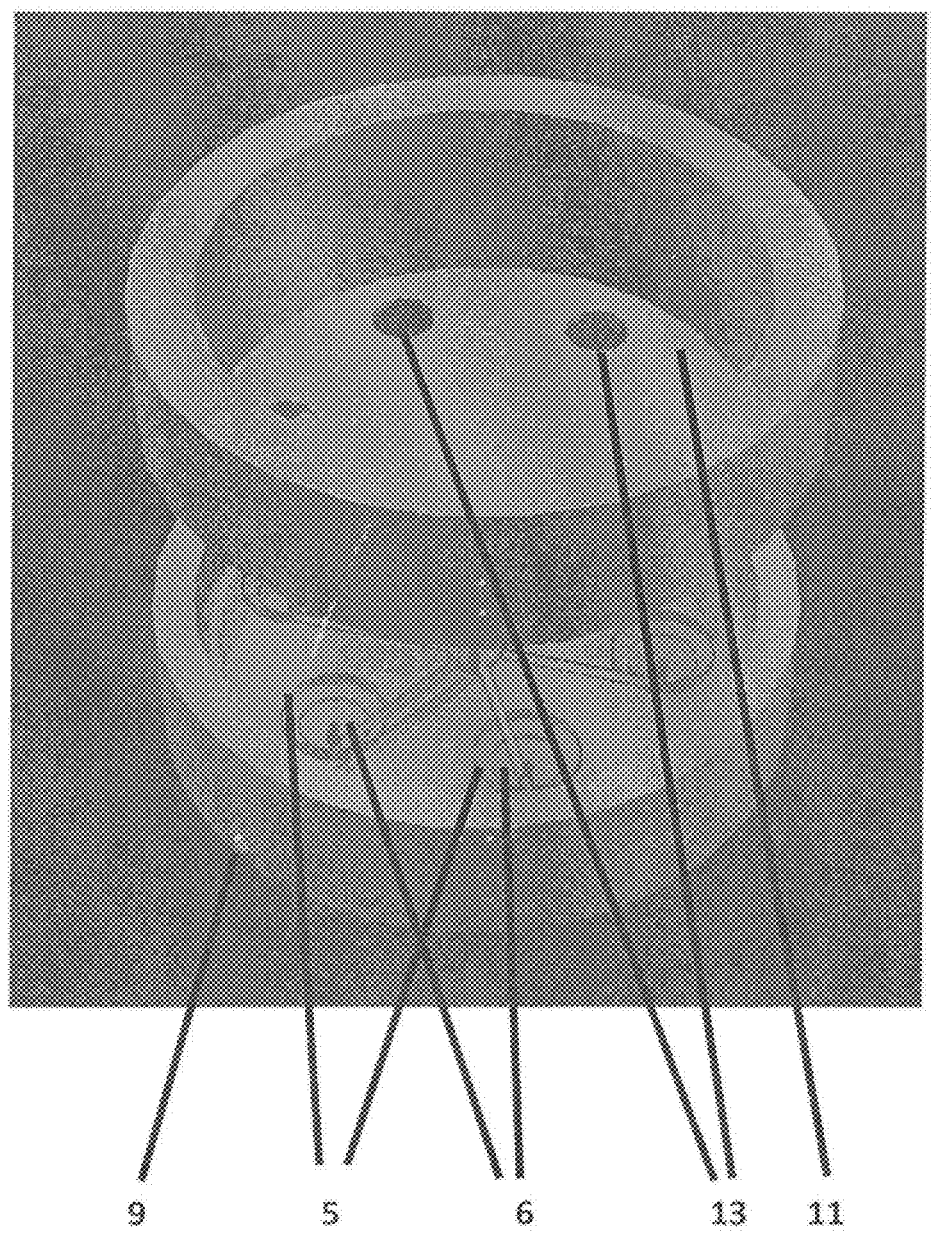
FIG. 17. Top side view of expanded bioreactor having a top portion and bottom portion. The bioreactor includes multiple equilibration and graft chambers.
Figure 18:
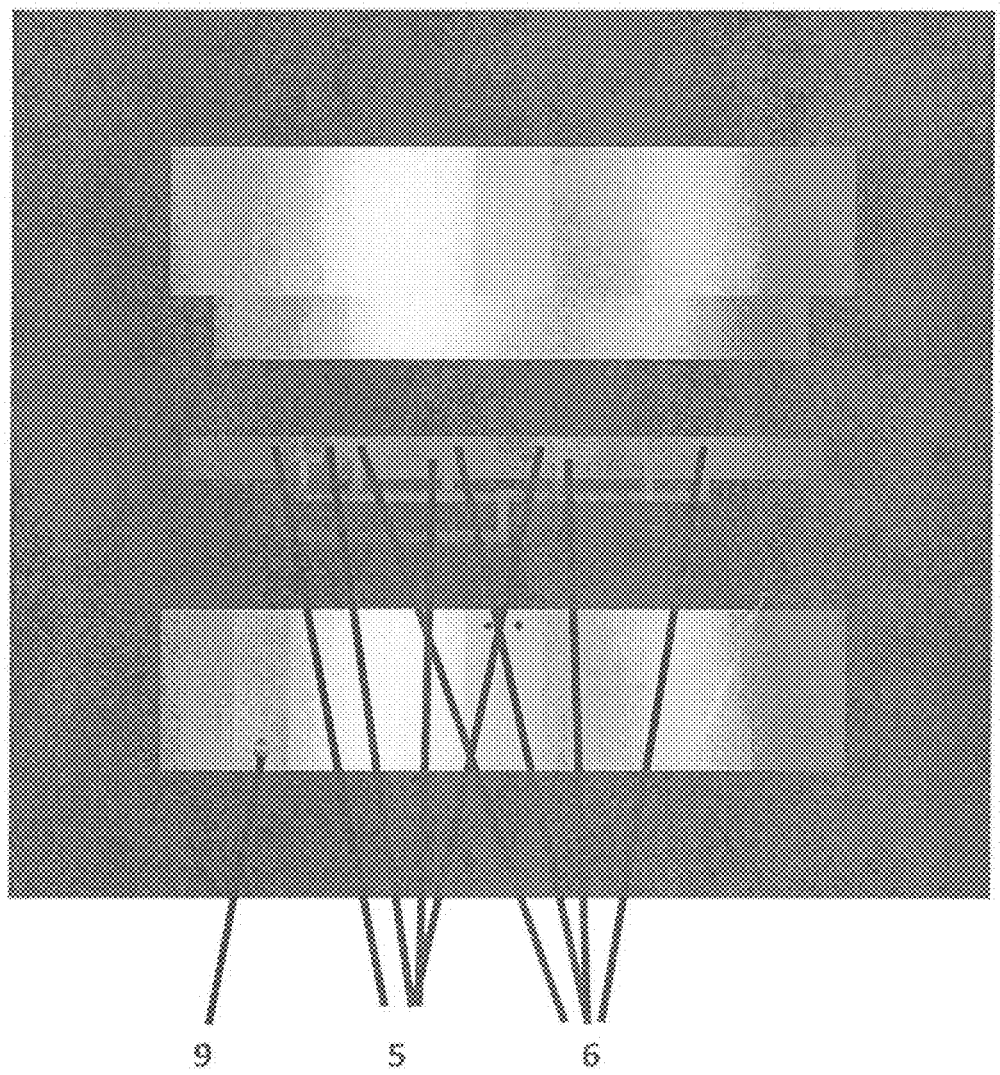
FIG. 18. Side view of expanded bioreactor of FIG. 17 having a top portion and bottom portion. The bioreactor includes multiple equilibration and graft chambers.
Figure 19:
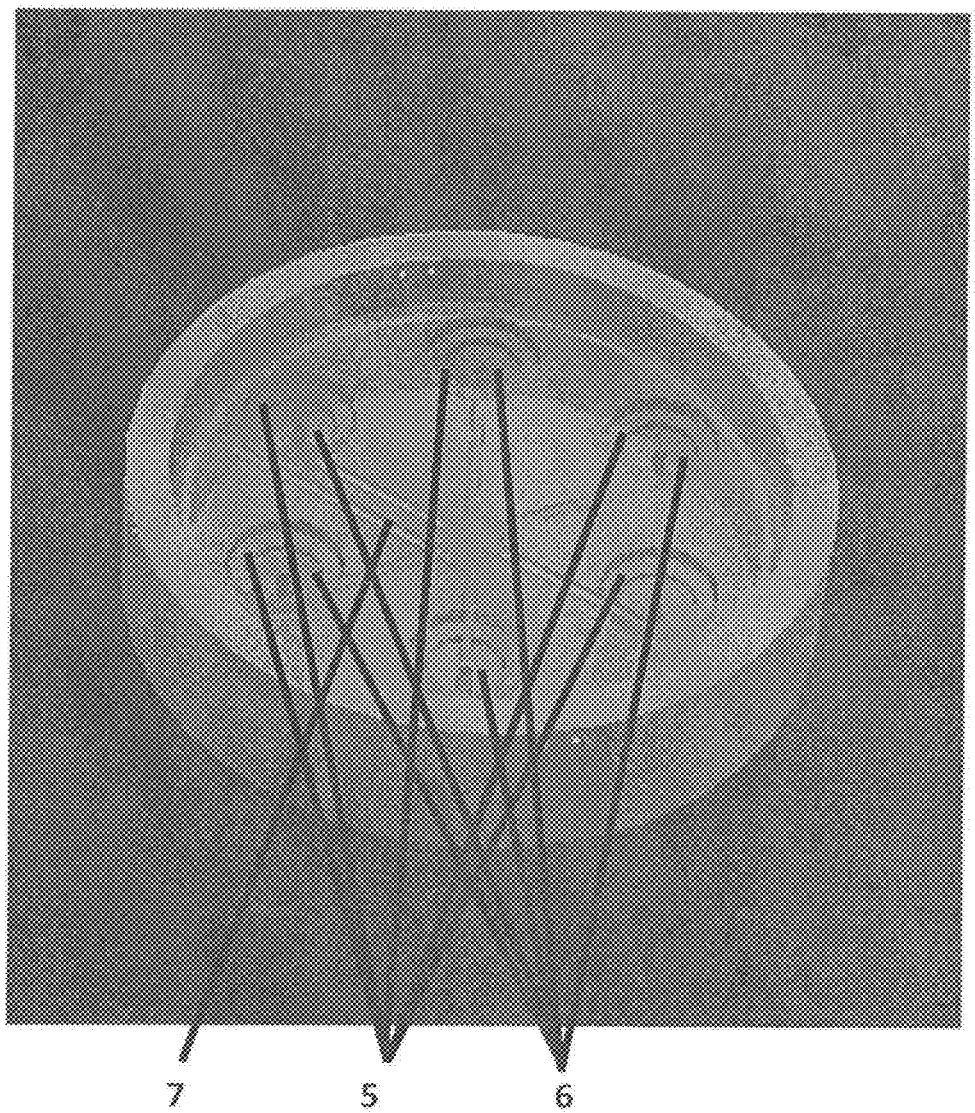
FIG. 19. Top side view of bottom portion of bioreactor of FIG. 17. The bioreactor includes multiple equilibration and graft chambers connected by a common perfusion channel.
Figure 20:
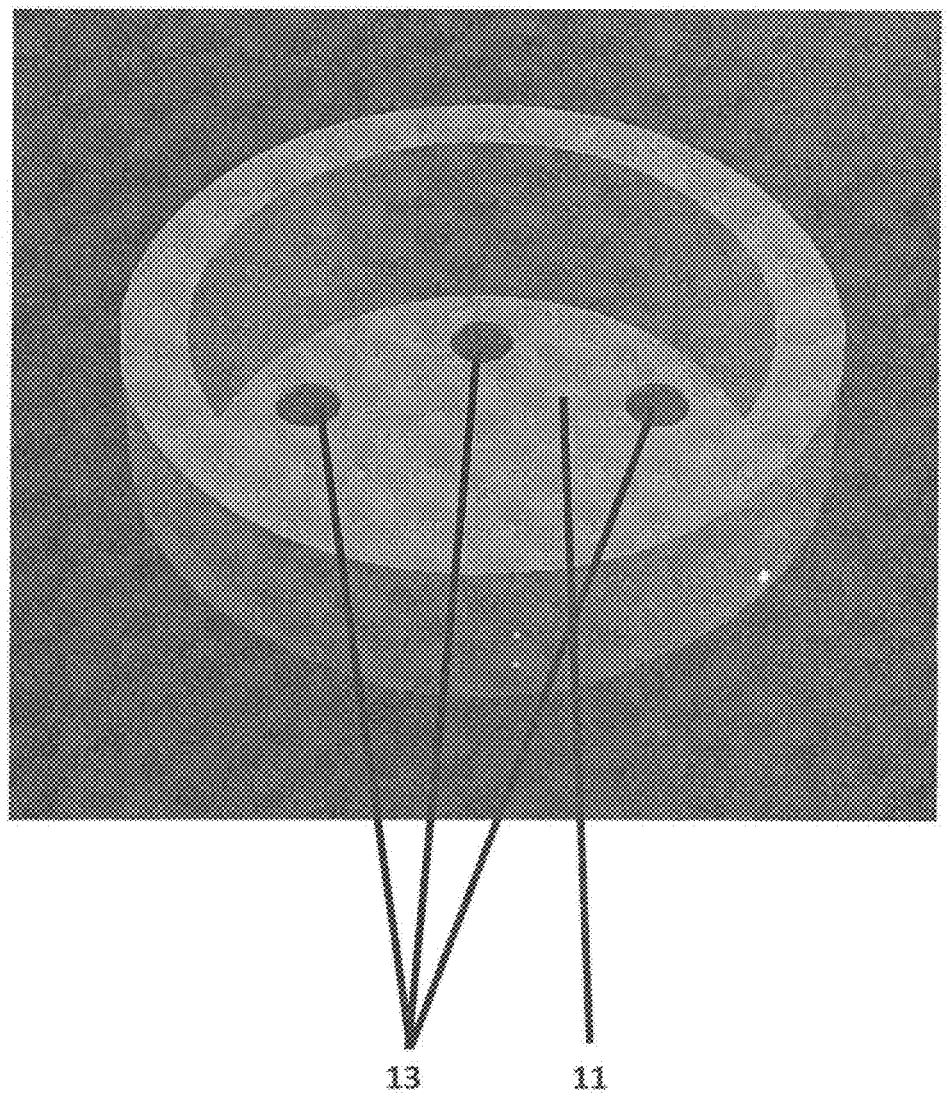
FIG. 20. Top side view of top portion of bioreactor of FIG. 17. The bioreactor includes multiple apertures fluidly connecting the fluid reservoir with each graft chamber.

In various embodiments, the equilibration chamber of the bioreactor of the present invention may include a tapered or flat surface with respect to the vertical inner side wall of the equilibration chamber. FIG. 16 shows equilibration chambers having both flat (90° with respect to the inner surface of the equilibration chamber) and tapered surfaces (150° and 105° with respect to the inner surface). In various embodiments, the taper may be any angle from 90-180° with respect to the inner side wall of the equilibration chamber, for example from about 90 to 95, 100, 105, 110, 115, 120, 125, 130, 135, 140, 145, 150, 155, 160, 165, 170, 175, 180, 185 or 90 degrees.

Perfusion Bioreactors

The present invention provides bioreactors, suitable for use in the preparation of tissue grafts and tissue graft segments as described herein. The bioreactors are perfusion bioreactors, for example, direct perfusion bioreactors. Perfusion bioreactors for tissue engineering applications are culture systems that typically comprise several elements, including, but not limited to one or more chambers where cell/scaffold constructs are placed (referred to herein as a "graft chamber"), a culture medium reservoir, a tubing circuit, and a pump enabling mass transport of nutrients and oxygen. Perfusion bioreactors may be broadly classified into indirect or direct systems, depending on whether the culture medium is perfused around or through the cell/scaffold constructs.

With direct perfusion bioreactors, cell/scaffold constructs are placed in a suitable graft chamber in a press-fit fashion so that the culture medium is forced to pass through the cell/scaffold construct, rather than around the cell/scaffold construct. Direct perfusion bioreactors have been used to engineer bone substitutes using a combination of different human osteocompetent cells and biomaterial scaffolds. Furthermore, in the case of bone engineering, studies demonstrate that direct perfusion of different combinations of cell/scaffold constructs can support cell survival and proliferation, and formation of mature bone-like tissue in vitro.

In some embodiments, the present invention provides bioreactors, such as direct perfusion bioreactors, and methods for designing and making such novel bioreactors. For example, in some embodiments models, such as digital models, of tissue portions or segments thereof, as described above, can be used to design and manufacture bioreactors that can accommodate one or more cell/scaffold constructs in a press-fit fashion under direct perfusion conditions. In some such embodiments CAD files of a tissue segment can be used to fabricate bioreactors, or graft chambers of bioreactors, or inserts for graft chambers of bioreactors, such that the bioreactor graft chamber has a size and geometry that is custom-designed to correspond to that of the tissue graft or tissue graft segment to be produced therein, and such that the scaffold and/or tissue graft/graft segment fits snugly within the bioreactor graft chamber in a press-fit configuration.

Perfusion bioreactors provided by the present invention, or the graft chambers or graft chamber inserts thereof, can be made out of any suitable material. Materials that are suitable for the manufacture of bioreactors, or inserts thereof, are known in the art and any such materials can be used. For example, in some embodiments bioreactors, or chambers or inserts thereof, may be made of an inert metal, such as stainless steel, or made of biocompatible plastic, or any other suitable material known in the art. The bioreactors may be made of material that is opaque, translucent or transparent.

In some embodiments, a bioreactor, bioreactor graft chamber, or bioreactor graft chamber insert is generated or customized using computer-assisted manufacturing. For example, in some such embodiments tissue segment files can be imported into CAM software to drive the fabrication or customization of bioreactors, bioreactor graft chambers, or bioreactor graft chamber inserts capable of accommodating geometrically defined scaffolds and/or tissue grafts or tissue graft segments using any suitable method known in the art, or a combination thereof. In some such embodiments, manufacturing or customization of the bioreactor may comprise using a rapid prototyping method, using a milling machine, using casting technologies, using laser cutting, and/or using three-dimensional printing. In some embodiments, manufacturing or customization of a bioreactor, bioreactor graft chamber, or bioreactor graft chamber insert may comprise using computer-numerical-control methods, such as when the manufacturing or customization process involves laser cutting or using a milling machine. For example, in some embodiments digital models generated using CAD software, for example, as described above may be processed to generate the appropriate G-Codes to drive a computer-numerical-control (CNC) milling machine (for example, Tormach, Bridgeport) and/or to select appropriate machining tool bits and/or program machining paths to cut the bioreactor, bioreactor graft chamber, or bioreactor graft chamber insert material into the desired shapes (e.g., complementary to the digital models of the tissue segments). In addition, digital drawing and simulation software can be used to optimize the design of bioreactors, bioreactor graft chambers, or bioreactor graft chamber inserts, and to drive the controlled manufacturing or customization thereof. In some embodiments bioreactors, bioreactor graft chambers, or bioreactor graft chamber inserts, can be designed based on digital models of tissues or tissue segments to facilitate culturing of cells, e.g., tissue-forming cells or other cells as described herein or known in the art, on scaffolds in order to produce a tissue graft or tissue graft segment having a size and shape corresponding to the complementary digital model of the tissue or tissue segment.

In FIGS. 1-11, 13 and 17-20, the bioreactors themselves, and certain elements such as the fluid reservoirs, prefusion equilibration and graft chambers are shown as having a circular shape. However, variations in both the shape and size of the bioreactors and any of the elements therein are also within the scope of the invention, and any suitably shaped and sized bioreactors or elements can be used. For example, one would appreciate that the equilibration and graft chambers may be circular, oval, elliptical, square, triangular, tear shaped, pear shaped, or any other desired geometric shape.

In some embodiments, the perfusion bioreactors may comprise multiple perfusion channels, equilibration chambers, graft chambers, and/or any other elements as required or needed for the collective culture of more than one bone segment (see FIG. 13). For example, a bioreactor according to the invention may be configured to accommodate the culture of one, two, three, four, five, six, seven, eight, nine, ten or more bone segments, as desired. Typically, a bioreactor will have one outlet port and one inlet port and one or more equilibration and graft chambers. FIGS. 17-20 depict a bioreactor in one embodiment of the invention which includes six equilibration and graft chambers which may be utilized to generate six bone segments simultaneously. The chambers are fluidly coupled to a single inlet and a single outlet.

Perfusion bioreactors according to the present invention may have various internal structural features as needed, for example, to facilitate manufacture or assembly of the bioreactors, and/or to maintain alignment of openings in the top and bottom portions such that fluid flows continuously through the bioreactor. For example, the bioreactors may have internal channels, grooves, indentations, holes, walls, bars, or pins to hold elements of the bioreactor in place inside the bioreactor and to maintain the various openings, channels and chambers in the correct position to facilitate fluid flow through the bioreactor and perfusion of the bone segment(s). In some embodiments, the bioreactors comprise a lid or cover over the fluid reservoir. In such embodiments, the reservoir cover is made of a material that allows gas exchange and oxygenation of fluid but prevents contamination of fluid in the reservoir. In some embodiments, the cover is attached to the bioreactor such that the cover can be opened and closed, for example by a hinge. In some embodiments, the cover is not attached to the bioreactor.

In some embodiments, the bioreactors of the invention may comprise a graft chamber that is designed or customized in order to accommodate a scaffold, tissue graft, or tissue graft segment of the desired shape and size. In one embodiment this may be achieved by designing or customizing the bioreactor itself such that it has a graft chamber having the desired shape and size. In another embodiment this may be achieved using a graft chamber insert that, when placed inside a bioreactor, produces a graft chamber that has the desired shape and size. In one embodiment, a bioreactor according to the present invention comprises a graft chamber of a size sufficient to accommodate a scaffold, tissue graft, or tissue graft segment having a thickness of about 0.3 millimeters to about 10 millimeters.

In some embodiments, the scaffold and/or tissue graft segment may be positioned in the graft chamber using a graft chamber insert, which may also be referred to herein as a "frame." As described above, frames or graft chamber inserts may be used to customize the size and shape of a graft chamber and position a scaffold and/or tissue graft segment in the graft chamber, as desired, for example in order to allow culture the tissue graft segment under direct perfusion, press-fit conditions to maximize the flow of fluid through the scaffold and/or tissue graft segment, and minimize the flow of fluid around the scaffold and/or tissue graft segment. In some embodiments the graft chamber may have a generic shape or size, but one or more frames or graft chamber inserts may be used to customize the size and shape (e.g., the internal size and shape) of the graft chamber, as desired, to accommodate the scaffold and/or tissue graft segment. Frames or graft chamber inserts may be made of any suitable material. For example, in some embodiments the frame and/or graft chamber insert may comprise, consist essentially of, or consist of, a biocompatible, non-toxic, moldable plastic, such as silicone or a silicone-like material. In some such embodiments, the frame and/or graft chamber insert may comprise polydimethylsiloxane (PDMS). Frames or graft chamber inserts may be designed and manufactured by any suitable method, including, but not limited to, the methods described herein.

In some embodiments the graft chamber may be a custom-shaped chamber(s) that accommodates the scaffold construct(s) until maturation of functional tissue. In one embodiment, a graft chamber is of a size sufficient to accommodate a segment of tissue (e.g. bone) having a thickness of about 0.3 millimeters to about 10 millimeters.

In some embodiments, a perfusion bioreactor provided by the invention may comprise sealing mechanisms and/or structures and/or configurations that prevent leakage or spillage of fluid from the bioreactor. For example, one or more gaskets or o-rings or the like (see, for example, FIGS. 4 and 6). Such elements can be made of any suitable material including without limitation rubber, silicone or plastic. In some embodiments, a bioreactor provided by the invention frames in graft and equilibration chambers to ensure secure fit of scaffold/bone segments; diffusion frits or other diffusion enhancing structures/materials can be inserted into the equilibration chamber to redirect fluid flow and optimize perfusion of bone segment. Such diffusion enhancing structures are preferably porous, and can have any suitable configuration.

The dimensions, geometry, configuration, size and/or shape of the bioreactor and any elements therein, including, for example, the graft and equilibration chambers, the size of perfusion hole, shape of the floor of the equilibration chamber, and thickness of the diffusion frits may be determined or defined using, for example, computational fluid dynamics software to simulate the hydrodynamic conditions inside a proposed configuration and experimental validation. In some embodiments of the invention, fluid turbulence inside the bioreactor may be minimized and homogenous perfusion of the cell/scaffold construct positioned in the graft chamber may be optimized.

Customized bioreactors of the present invention may be generated using a number of methods. Additionally, the bioreactors may be generated from a single unitary material, such as a block, or multiple pieces such as those depicted in the Figures as having a top portion and bottom portion. Methods of manufacture may those conventional methods known in the art, such as, but in no way limiting, three-dimensional printing, casting, milling, laser cutting, rapid prototyping, or any combination thereof.

In some embodiments bioreactors, bioreactor graft chambers, and graft chamber frames or inserts, as provided by the present invention, can be designed and manufactured as described herein, for example using computer-aided design (CAD) and computer-aided manufacture (CAM) methods. However, a person having ordinary skill in the art will appreciate that a variety of other methods may be used to generate and customize bioreactors, bioreactor graft chambers, and bioreactor graft chamber frames or inserts according to the present invention.

Size and Shape Variations

As used herein, the terms "corresponding to" and "correspond to," when used in relation to any aspect of the present invention where size and shape matching of two or more elements is contemplated, can mean any of the size and shape variations described in this section. Such variations described in this section can apply equally to all aspects of the present invention where size and shape matching of two or more elements is contemplated. Such elements include, tissue portions, tissue models, tissue grafts, model segments, tissue segments, bioreactors, bioreactor chambers (e.g. bioreactor graft chambers) and inserts (e.g. bioreactor graft chamber inserts), scaffolds, scaffold precursors, cell/scaffold constructs, and any other element of the invention as described in the present application.

The illustrative embodiments in this section describe size and shape variations between two elements of the invention—a first element and a second element. However the present invention contemplates that any desired number of elements, such as three, four, five or more, may have corresponding sizes and shapes as described herein. Numerous combinations of elements are envisioned and are within the scope of the present invention, including, but not limited to those described elsewhere in the present specification and those that combine any one or more of the elements described above or elsewhere in the application. The variations described in this section apply equally to any such combinations where elements may be matched by size and shape.

In some embodiments where a first element has a size and shape corresponding to a second element, the first element has the same, or about the same, or approximately the same size and shape as the second element. In some embodiments where a first element has a size and shape corresponding to a second element, the first element has a similar or complementary size and shape as the second element.

In some embodiments where a first element has a size and shape corresponding to the size and shape of a second element, the size and shape of the first element varies by plus or minus 0.1%, 0.2%, 0.3%, 0.4%, 0.5%, 0.6%, 0.7%, 0.8%, 0.9%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, or 20% of the size and shape of the second element.

For example, in some embodiments the present invention utilizes a three-dimensional model having a size and shape corresponding to a particular tissue portion (e.g. a portion of tissue to be constructed, replaced, or repaired). In some embodiments the present invention utilizes a three-dimensional model segment having a size and shape corresponding to a cell scaffold, a bioreactor, a graft chamber, a graft chamber insert, and/or a tissue segment. In some embodiments the present invention provides a cell scaffold or cell scaffold precursor having a size and shape corresponding to a tissue portion model, a model segment, a bioreactor, a graft chamber, a graft chamber insert, a tissue segment, and/or a tissue graft. In some embodiments the present invention provides a bioreactor having a size and shape corresponding to a tissue portion model, a model segment, a scaffold, a graft chamber, a graft chamber insert, a tissue segment, and/or a tissue graft. In some embodiments the present invention provides a bioreactor graft chamber or a bioreactor graft chamber insert having a shape and size corresponding to tissue portion model, a model segment, a tissue segment, and/or a tissue graft. In some embodiments the present invention provides a tissue segment having a size and shape corresponding to a model segment, a bioreactor, a scaffold, a graft chamber, and/or a graft chamber insert. In some embodiments the present invention provides a tissue graft having a size and shape corresponding to a particular tissue portion and/or a three-dimensional model of a particular tissue portion.

Acceptable variations in size and shape can also be determined based on the desired function of the two or more elements to be matched by size and shape. In some embodiments where a first element has a size and shape corresponding to the size and shape of a second element, the first and second elements can have any suitable size and shape suitable that allows one or both elements to perform a desired function and/or have a desired property. For example, in some such embodiments a tissue graft has a size and shape corresponding to a portion of tissue to be repaired provided that the tissue graft is capable of suitably repairing the tissue portion. In some such embodiments a cell scaffold has a size and shape corresponding to a graft chamber or graft chamber insert provided that the cell scaffold fits into the graft chamber or graft chamber insert under press fit conditions.

In addition, a person having ordinary skill in the art will appreciate that other acceptable variations in size and shape can be determined and that such variations are intended fall within the scope of the present invention.

Three-Dimensional Models

Figure 15A:
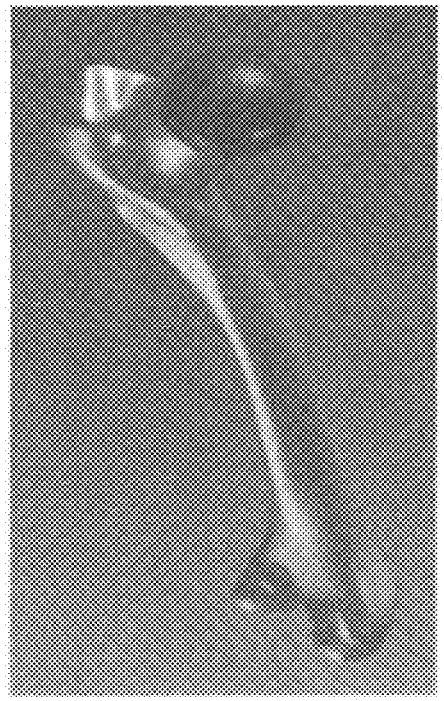
FIGS. 15A-15B.
Figure 15B:
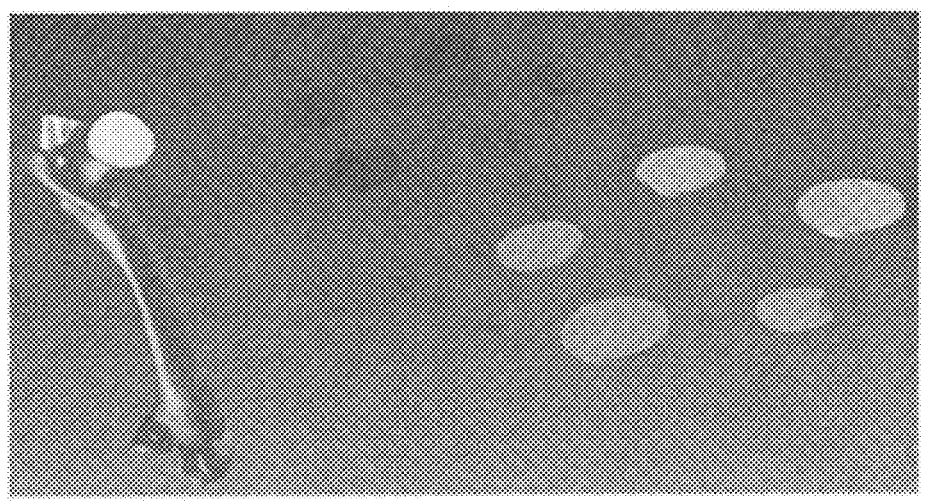

In some embodiments of the present invention, three-dimensional models of a particular tissue or tissue portion may be generated and/or used, for example to serve as a template for the production of a tissue graft or tissue graft segment, and/or to serve as a template for the production of a scaffold material to be used in the manufacture of such a tissue graft or tissue graft segment, and/or to serve as a template for the production of a bioreactor, bioreactor chamber, or bioreactor chamber insert that could be used in the production of a tissue graft or tissue graft segment (see, e.g., FIGS. 15A-15B). In some embodiments such three-dimensional models are digital models, such as digital models that represent the three-dimensional shape and size of a tissue portion of interest. For example, three-dimensional models or images, such as digital models or images of structures inside the body, can be generated by any suitable method known in the art, including, for example, computed tomography (CT) (including small-scale CT such as micro-CT) which uses x-rays to make detailed pictures of internal body structures and organs. In some embodiments medical imaging technologies can be used to generate a digital model of a desired tissue portion, for example a tissue portion comprising a defect, such as a skeletal defect, and that digital model can then be used to facilitate the manufacture of a tissue graft, and/or one or more tissue graft segments, for example by enabling the production of a scaffold material and/or bioreactor that is custom designed to be used in the manufacture of the desired tissue graft or tissue graft segment. A model of a tissue portion will preferably be anatomically accurate, having dimensions, geometry, size and shape that correspond to the physical tissue portion and/or the desired tissue graft. In some embodiments, the portion of tissue may comprise a defect, such as a traumatic or pathological defect. In some embodiments, such defect can be repaired using a tissue graft prepared according to the present invention. Digital models of tissue portions can be created using any suitable computer-aided design (CAD) software, such as AUTOCAD®, SOLIDWORKS®, PROE®, or CREO®. In some embodiments a digital model of a tissue portion can be edited and segmented/partitioned into two or more smaller sub-parts or segments (which may be referred to as "model segments" or "model portions"), for example representing tissue graft segments that can be prepared according to the present invention, and/or representing scaffold materials or bioreactor chambers that can be used for the preparation of such tissue graft segments. The thickness of the model segments can be selected such that a tissue graft segment having the same thickness could be effectively perfused in a bioreactor of the present invention. Thus, in some embodiments, a model segment, and/or a corresponding tissue graft segment (e.g. a bone graft segment), has a thickness or a maximum thickness of about one centimeter or less. In some embodiments, the model segment and/or the corresponding tissue graft segment has a thickness or a maximum thickness of about 0.3 millimeters to about 10 millimeters, or about 0.3 millimeters to about 5 millimeters, or about 0.3 millimeters to about 1 millimeter. In some embodiments, the model segment and/or the corresponding tissue graft segment has a thickness of about 0.3, about 0.5, about 1, about 1.5, about 2, about 2.5, about 3, about 3.5, about 4, about 4.5, about 5, about 5.5, about 6, about 6.5, about 7, about 7.5, about 8, about 8.5, about 9, about 9.5, or about 10 millimeters.

The models, such as digital models, described herein can be used to design and manufacture customized bioreactors as described herein and/or customized scaffolds to grow physical tissue graft segments having a size and shape corresponding to the complementary models. In the case of digital models, the models or model segments can be created using, or converted into, any suitable file formats, for example, IGES or SLT formats, and can be created using, or imported into, any suitable computer-aided manufacturing (CAM) software, for example, SPRUTCAM®. Manufacture of custom bioreactors and scaffolds is further described herein.

Digital models of tissues, and segments thereof, provided by the invention can be generated, edited and otherwise manipulated as described herein. In addition, a person having ordinary skill in the art will appreciate that any other suitable methods may be used to generate, edit or otherwise manipulate digital models of tissues or segments thereof as described herein.

Cell Scaffolds

In some embodiments, the present invention provides scaffolds suitable for use in the preparation of tissue grafts and/or tissue graft segments, for example as described herein. Scaffolds can be made of any suitable material having appropriate pore sizes, porosity and/or mechanical properties for the intended use. In some embodiments cell scaffolds provided by the invention may have a three-dimensional structure and can be made of any compliant biomaterial with appropriate porosity, pore size and mechanical properties. Such suitable materials will typically be non-toxic, biocompatible and/or biodegradable, and capable of infiltration by cells of the desired tissue graft type, for example bone-forming cells in the case of bone tissue grafts. Non-limiting examples of such materials include de-cellularized tissue (such as de-cellularized bone), materials that comprise or one or more extracellular matrix ("ECM") components such as collagen, laminin, and/or fibrin, and natural or synthetic polymers or composites (such as ceramic/polymer composite materials). In some embodiments the scaffold material may be capable of being absorbed by cells (e.g., resorbable materials), while in other embodiments non-resorbable scaffold materials may be used. In some embodiments, the scaffold may comprise, consist of, or consist essentially of, any of the above-listed materials, or any combination thereof.

In some embodiments, the dimensions and geometry of a scaffold correspond to that of a three-dimensional model, such as a digital model, of a tissue portion or tissue segment, and/or correspond to that of the desired tissue graft of tissue graft segment, as described above. In some embodiments the dimensions and geometry of a scaffold can be designed or selected based on such a model in order to facilitate culturing of cells, e.g., tissue-forming cells or other cells as described herein, on the scaffold within a bioreactor, as described herein, for example in order to produce a tissue graft or tissue graft segment having a size and shape corresponding to a model or model segment. In some embodiments, scaffolds may be designed to fit into a bioreactor chamber or graft chamber insert of suitable size and shape to allow direct perfusion of the scaffold and the cells therein (e.g. during the process of producing the tissue graft and/or tissue graft segment) under press-fit conditions. FIGS. 12A-12B show illustrative scaffolds as provided herein.

In some embodiments cells, for example bone pregenitor cells, may be seeded onto the scaffold, then the cell/scaffold structure may be placed or inserted into the graft chamber of a perfusion bioreactor. The scaffold may be positioned using forceps or the like. In some embodiments, fabricated scaffolds are sterilized and/or conditioned in culture medium prior to cell seeding. In some embodiments cells may grow on or within the scaffold under direct perfusion conditions in the bioreactor until maturation of functional tissue, e.g. bone tissue.

In some embodiments, the scaffold is generated or customized using computer-assisted manufacturing (CAM). For example, a tissue model segment file can be used with, CAM software to drive the fabrication of geometrically defined scaffolds using any suitable method known in the art, or a combination thereof, for example, computer-controlled milling methods, rapid prototyping methods, laser cutting methods, three-dimensional printing, and/or casting technologies. In some embodiments, manufacturing of the scaffold comprises using rapid prototyping, a milling machine, casting technologies, laser cutting, and/or three-dimensional printing, or any combination thereof. In some embodiments, manufacturing of the scaffold comprises using computer-numerical-control, such as when the manufacturing comprises laser cutting or using a milling machine. For example, digital models, such as those generated using CAD software as described above, can be processed to generate the appropriate codes (such as "G-Codes") to drive a computer-numerical-control (CNC) milling machine (for example, Tormach, Bridgeport) and to select appropriate machining tool bits and program machining paths to cut the scaffold material into the desired shapes and sizes (e.g., corresponding to that of a digital models of a tissue segment).

While scaffolds provided by the invention can be designed and manufactured as described herein, a person having ordinary skill in the art will appreciate that a variety of other methods of designing and manufacturing may be used to generate scaffolds according to the present invention.

Cells

Any suitable or desired type of cell or cells may be used in the preparation of tissue grafts or tissue graft segments in accordance with the present invention, as described herein.

Typically the selected cell(s) will be capable of forming the desired tissue graft (for example, for a vascularized bone graft, mesenchymal progenitor cells and endothelial progenitor cells or any other cell types suitable for or capable of forming bone and blood vessels, as further described herein), or any cell(s) capable of differentiating into the desired tissue-forming cell(s) (for example, a pluripotent cell). Non-limiting examples of cells that may be used include pluripotent cells, stem cells, embryonic stem cells, induced pluripotent stem cells, progenitor cells, tissue-forming cells, or differentiated cells.

The cells used may be obtained from any suitable source. In some embodiments, the cells may be human cells. In some embodiments, the cells may be mammalian cells, including, but not limited to, cells from a non-human primate, sheep, or rodent (such as a rat or mouse). For example, cells may be obtained from tissue banks, cell banks or human subjects. In some embodiments, the cells are autologous cells, for example, cells obtained from the subject into which the prepared tissue graft will be subsequently transplanted, or the cells may be derived from such autologous cells. In some embodiments, the cells may be obtained from a "matched" donor, or the cells may be derived from cells obtained from a "matched" donor. For cell and tissue transplants, donor and recipient cells can be matched by methods well known in the art. For example, human leukocyte antigen (HLA) typing is widely used to match a tissue or cell donor with a recipient to reduce the risk of transplant rejection. HLA is a protein marker found on most cells in the body, and is used by the immune system to detect cells that belong in the body and cells that do not. HLA matching increases the likelihood of a successful transplant because the recipient is less likely to identify the transplant as foreign. Thus, in some embodiments of the present invention, the cells used are HLA-matched cells or cells derived from HLA-matched cells, for example, cells obtained from a donor subject that has been HLA-matched to the recipient subject who will receive the tissue graft. In some embodiments the cells used may be cells that have been modified to avoid recognition by the recipient's immune system (e.g. universal cells). In some such embodiments the cells are genetically-modified universal cells. For example, in some embodiments the universal cells may be MHC universal cells, such as major histocompatibility complex (MHC) class I-silenced cells. Human MHC proteins are referred to as HLA because they were first discovered in leukocytes. Universal cells have the potential to be used in any recipient, thus circumventing the need for matched cells.

In some embodiments, the cells used in making the tissue grafts described herein, include pluripotent stem cells, such as induced pluripotent stem cells (iPSCs). In some such embodiments, the pluripotent stem cells may be generated from cells obtained from the subject (i.e. autologous cells) that will receive the tissue graft. In other such embodiments, the pluripotent stem cells may be generated from cells obtained from a different individual, i.e., not the subject that will receive the tissue graft (i.e. allogeneic cells). In some such embodiments, the pluripotent stem cells may be generated from cells obtained from a different individual, i.e., not the subject that will receive the tissue graft, but where that different individual is a "matched" donor, for example as described above. In some embodiments, the cells used are differentiated cells, such as bone cells. In some embodiments, the differentiated cells are derived from pluripotent stem cells, such as induced pluripotent stem cells. In some embodiments, the differentiated cells are derived by transdifferentiation of differentiated somatic cells, or by transdifferentiation of pluripotent cells (such as pluripotent stem cells or induced pluripotent stem cells), for example induced pluripotent stem cells generated from somatic cells.

A pluripotent stem cell is a cell that can (a) self-renew and (b) differentiate to produce cells of all three germ layers (i.e. ectoderm, mesoderm, and endoderm). The term "induced pluripotent stem cell" encompasses pluripotent stem cells, that, like embryonic stem cells (ESC), can be cultured over a long period of time while maintaining the ability to differentiate into cells of all three germ layers, but that, unlike ES cells (which are derived from the inner cell mass of blastocysts), are derived from somatic cells, that is, cells that had a narrower, more defined potential and that in the absence of experimental manipulation could not give rise to cells of all three germ layers. iPSCs generally have an hESC-like morphology, growing as flat colonies with large nucleo-cytoplasmic ratios, defined borders and prominent nuclei. In addition, iPSCs generally express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. In addition, iPSCs, like other pluripotent stem cells, are generally capable of forming teratomas. In addition, they are generally capable of forming or contributing to ectoderm, mesoderm, or endoderm tissues in a living organism.

Illustrative iPSCs include cells into which the genes Oct-4, Sox-2, c-Myc, and Klf have been transduced. Other exemplary iPSCs are cells into which OCT4, SOX2, NANOG, and LIN28 have been transduced. One of skill in the art would know that various different cocktails of reprogramming factors can be used to produce iPSCs, such as factors selected from the group consisting of OCT4, SOX2, KLF4, MYC, Nanog, and Lin28. The methods described herein for producing iPSCs are illustrative only and are not intended to be limiting. Rather any suitable methods or cocktails of reprogramming factors known in the art can be used. In embodiments where reprogramming factors are used, such factors can be delivered using any suitable means known in the art. For example, in some embodiments any suitable vector, such as a Sendai virus vector, may be used. In some embodiments reprogramming factors may be delivered using modified RNA methods and systems. A variety of different methods and systems are known in the art for delivery of reprogramming factors and any such method or system can be used.

Any culture medium suitable for culture of cells, such as pluripotent stem cells, may be used in accordance with the present invention, and several such media are known in the art. For example, a culture medium for culture of pluripotent stem cells may comprise Knockout DMEM, 20% Knockout Serum Replacement, nonessential amino acids, 2.5% FBS, Glutamax, beta-mercaptoethanol, 10 ng/microliter bFGF, and antibiotic. The employed medium may also be a variation of this medium, for example without the 2.5% FBS, or with a higher or lower % of knockout serum replacement, or without antibiotic. The employed medium may also be any other suitable medium that supports the growth of human pluripotent stem cells in undifferentiated conditions, such as mTeSR (available from STEMCELL Technologies), or NUTRISTEM® (available from Stemgent), or ES medium, or any other suitable medium known in the art. Other exemplary methods for generating/obtaining pluripotent stem cells from a population of cells obtained from a subject are provided in the Examples of the present application.

In some embodiments, pluripotent stem cells are differentiated into a desired cell type, for example, a bone-forming cell or a blood vessel-forming cell, or any other desired cell type. Differentiated cells provided by the invention can be derived by various methods known in the art using, for example, adult stem cells, embryonic stem cells (ESCs), epiblast stem cells (EpiSCs), and/or induced pluripotent stem cells (iPSCs; somatic cells that have been reprogrammed to a pluripotent state). Methods are known in the art for directed differentiation or spontaneous differentiation of pluripotent stem cells, for example by use of various differentiation factors. Differentiation of pluripotent stem cells may be monitored by a variety of methods known in the art. Changes in a parameter between a stem cell and a differentiation factor-treated cell may indicate that the treated cell has differentiated. Microscopy may be used to directly monitor morphology of the cells during differentiation.

In each of the embodiments of the invention, any suitable or desired types of cells can be used to produce the tissue grafts and tissue graft segments described herein, including, but not limited to, pluripotent stem cells or progenitor cells or differentiated cells. In some embodiments, the pluripotent stem cells may be induced pluripotent stem cells. In embodiments where induced pluripotent stem cells are used, such cells may be derived from differentiated somatic cells obtained from a subject, for example by contacting such differentiated somatic cells with one or more reprogramming factors. In some embodiments, pluripotent cells may have been induced toward a desired lineage, for example, mesenchymal lineage or endothelial lineage. In some embodiments, the differentiated cells can be any suitable type of differentiated cells. In some embodiments, the differentiated cells may be derived from pluripotent stem cells (such as induced pluripotent stem cells), for example by contacting such pluripotent cells with one or more differentiation factors. In some embodiments, the differentiated cells may be derived by trans-differentiation of another differentiated cell type, for example by contacting the cells with one or more reprogramming factors. In the various embodiments of the present invention involving differentiated cells, such differentiated cells may be any desired differentiated cell type, including, but not limited to, bone cells and blood vessel cells.

Cell/Scaffold Constructs

Any suitable or desired type of cell, such as the cell types described herein, can be applied to or seeded onto a scaffold to prepare tissue graft or tissue graft segment according to the present invention.

In some embodiments, cells may be in a differentiated state prior to being applied to a scaffold. For example, in some embodiments differentiated cells may be obtained and used directly. Similarly, in some embodiments non-differentiated cells may be cultured according to any suitable method known in the art, such as in a culture dish or multi-well plate or in suspension, for a suitable period or length of time, for example, until desired levels of cell growth or differentiation or other parameters are achieved, then the differentiated cells may be transferred to the scaffold and subsequently the cell/scaffold construct is inserted into a bioreactor to facilitate development of a tissue graft or tissue graft segment. In some embodiments, non-differentiated cells (for example, stem cells (such as iPSCs) or progenitor cells) may be applied to the scaffold. In such embodiments, the non-differentiated cells may undergo differentiation while being cultured on the scaffold.

In some embodiments, two or more different cell populations may be seeded onto a scaffold to prepare a cell/scaffold construct. For example, in some embodiments both bone-forming cells and blood vessel-forming cells may be seeded onto a scaffold and co-cultured for the preparation of a vascularized bone graft. In some embodiments, the two or more populations of cells are co-cultured on the scaffold for a suitable period of time, for example, until desired levels of growth or differentiation or other parameters are achieved, before the cell/scaffold construct is inserted into the bioreactor. Populations of cells may comprise, consist essentially of, or consist of, any desired type of cell in any stage of growth or differentiation, and any combinations thereof. For example, in some embodiments, each cell population may comprise cells capable of forming a different tissue, for example for the preparation of a vascularized bone graft, a first population containing cells capable of forming bone, such as mesenchymal progenitor cells, and a second population containing cells capable of forming blood vessels, such as endothelial progenitor cells. In some embodiments, each population of cells may comprise cells capable of forming the same tissue (e.g., bone) but each population of cells may be at different stages of differentiation (e.g., mesenchymal stem cells and bone marrow stromal cells). Populations of cells to be co-cultured may be applied to a scaffold at the same time or at different times, as desired. Where two or more populations of cells are applied at different times, the sequence or order of co-culture (e.g., which population is applied to the scaffold first, which population is applied to the scaffold second, etc.) may be selected as desired, for example depending on the cell types being used, the state or growth or differentiation of the populations of cells, or any other parameters, as desired. Where two or more populations of cells are to be applied to the scaffold, they can be applied at any suitable cell ratio, as desired. For example, in some embodiments two different populations of cells may be seeded at a ratio of about 1:1, or any ratio from about 2:8 to about 8:2. In some embodiments, the cell populations may be seeded at a ratio of about 2:8, about 3:7, about 4:6, about 5:5, about 6:4, about 7:3, or about 8:2.

A cell/scaffold construct may be transferred to a bioreactor of the present invention at any suitable point, for example, immediately after seeding with cells, following a certain period of cell culture following seeding, after the seeded cells have reached a desired state of differentiation or any other desired state, as desired. In some embodiments the cell/scaffold construct is inserted into a bioreactor and cultured under press fit conditions to allow formation of a tissue graft or tissue graft segment. Tissue/graft development can be assessed using any suitable qualitative or quantitative methods known in the art, including but not limited to histological and immunohistochemical examination, biochemical assays, high-resolution characterization techniques (e.g., SEM, FIB-TEM, Tof-SIMS), imaging procedures (e.g., CT or microCT) and mechanical testing (e.g., Young's modulus, tensile and compressive strength).

A person having ordinary skill in the art will recognize that countless variations and combinations of cells and culture methods will fall within the scope of the present invention. For example, cell culture methods, including cell seeding ratios, concentration of differentiation factors and sequence of co-culture, will typically be determined according to the desired cell type being used or the tissue graft being prepared.

Tissue Grafts, and Assembly and Use Thereof

In some embodiments, the present invention provides tissue grafts, such as bone grafts, that are assembled from multiple tissue graft segments generated in a bioreactor of the present invention. The present invention also provides methods of making such tissue grafts. Such methods may be referred to as segmental additive tissue engineering (SATE) methods. In the case of bone grafts in particular, such methods may be referred to as segmental additive bone engineering (SABE) methods. At any suitable point, for example when a tissue graft segment having the desired properties has been produced, tissue graft segments can be removed from the bioreactor in which they are produced and multiple tissue graft segments can be assembled together to form a tissue graft having the desired size and shape, for example a size and shape corresponding to the tissue portion to be replaced.

Assembled tissue graft segments can be secured or attached together by any suitable means or method capable of maintaining the intended assembly of the segments. For example typically, such securing means or methods will be non-toxic, biocompatible and/or resorbable (e.g., capable of being absorbed by the body), for example, where the assembled tissue graft will be transplanted into a subject. For example, in some embodiments, the tissue graft segments may be secured to each other using an adhesive, stitches or sutures, staples, plates, pins and holes, screws, bolts, or the like, as desired. In some embodiments, the means used to secure the tissue segments together are biocompatible or resorbable or both.

In some embodiments, where an adhesive is used to secure the graft segments to each other, the adhesive may be a biocompatible glue, for example, a biocompatible polymer glue such as NOVOSORB® (PolyNovo Biomaterials, Melbourne) or any gel, liquid, rubber-like substance, or other biocompatible adhesive material capable of securing together two or more tissue graft segments. For example, in the case of bone grafts, exemplary bone glues that can be used to secure bone graft segments to each other include, but are not limited to, polymer-based or polymeric bone glues such as polyurethane-based and polymethylmethacrylate-based bone glues. In some embodiments, the adhesive may be a tape, for example, a surgical tape. In some embodiments, tissue graft segments may be secured to each other using one or more plates, pins, screws, bolts, staples, stitches, sutures, or the like, for example made of plastic, metal (for example, titanium) or any other suitable material. In some embodiments such pins, screws, bolts, staples, stitches, sutures, or the like may be manufactured using 3D printing or any other suitable method known in the art.

In some embodiments, various different means and/or methods to secure the assembled tissue graft segments together may be used in combination, for example, to reinforce the connection between the assembled tissue graft segments and/or to attach or anchor or secure the tissue graft to the host tissues, such as where a tissue graft is transplanted into a subject. For example, in some embodiments engineered bone graft segments as described herein can be assembled together using both a biocompatible bone glue and metallic or resorbable pins.

Following assembly and securing together of the tissue graft segments, the resulting tissue graft can be transplanted into a subject, where it may also be anchored to the subject's tissues (such as surrounding bone in the case of a bone graft). In some embodiments, the methods and compositions provided by the present invention may be used to engineer tissue grafts for clinical applications, including therapeutic and/or cosmetic applications. Non-limiting examples of such applications include repair or replacement of a tissue defect or damage or tissue loss, tissue reconstruction or rebuilding, tissue reinforcement (e.g., to prevent or delay progression of tissue damage or loss of tissue) or to assist in the implantation of surgical devices (e.g., bone grafts can be used to help bone heal around surgically implanted devices such as joint replacements, plates or screws). In some embodiments, a subject has a tissue defect or tissue loss caused by injury, disease, birth defect, trauma or infection.

In some embodiments, the invention provides a method of repairing or replacing a tissue defect, tissue loss or tissue damage, comprising transplanting a tissue graft according to the present invention into a subject so as to repair or replace the tissue defect, tissue loss or tissue damage in the subject. In some embodiments, the tissue graft will have a size and shape corresponding to that of the tissue being repaired or replaced. Tissue grafts according to the present invention can be prepared using the segmental additive tissue engineering or SATE methods provided herein. Thus, in some embodiments, a tissue graft according to the present invention may comprise, consist of, or consist essentially of, two or more tissue graft segments, wherein the tissue graft segments have a thickness of less than about 1 centimeter, or a thickness of about 0.3 millimeters to about 10 millimeters. In some embodiments, such a tissue graft may be an autograft (also referred to as an autogenous, autogenic or autologous graft), such as where the subject's own cells or tissue (e.g., autologous cells or tissue) are used to generate the tissue graft. In some embodiments, the tissue graft is an allograft (e.g., the tissue graft is generated from cells or tissues obtained from a donor subject of the same species as the recipient subject), such as where the donor and recipient subjects have been matched, for example, by HLA-matching. In some embodiments, the tissue graft is a xenograft (e.g., the tissue graft is generated from cells or tissues obtained from a donor subject of a different species as the recipient subject). For example, a tissue graft comprising human tissue may be transplanted into a non-human mammal, such as a sheep, for example for performing certain in vivo testing, etc.

A tissue graft prepared according to the present invention and transplanted into a subject can be anchored or attached or secured to existing structures (e.g., tissue) in the subject by any suitable method capable of securing tissue, such as described above. In some embodiments, the transplanted tissue graft is secured by an adhesive, stitches or sutures, staples, plates, pins or the like. In some embodiments, the means to secure the tissue graft inside the subject's body will be biocompatible or resorbable or both.

Subjects

In some embodiments the cells used in producing the tissue grafts of the present invention may be obtained from or derived from any subject, as needed or as desired. In some embodiments the methods (e.g. treatment methods) and compositions (e.g., tissue grafts) provided by the present invention may be used in any subject, as needed or as desired (for example, to repair a pathological or traumatic tissue defect, or for cosmetic or reconstructive purposes). In some embodiments, the subject is a human. In some embodiments, the subject is a mammal including but not limited to a non-human primate, sheep, or rodent (such as a rat or mouse). In some embodiments, a first subject is a donor subject and a second subject is a recipient subject. In some such embodiments the donor subject, or cells of the donor subject, may be matched to the recipient subject or cells of the recipient subject, for example, by HLA-type matching.

Model Systems and Screening Methods

In some embodiments, the present invention provides model systems for studying various biological processes or biological properties, and screening methods for testing the effects of various agents on such biological processes and/or biological properties.

In some embodiments, the present invention provides a model system comprising a tissue graft according to the present invention. For example, in some embodiments the present invention provides a model system comprising a tissue graft according to the present invention that has been implanted into a subject. Model systems provided by the invention can be used for various purposes such as but not limited to screening or testing materials for implantation and to study diseases under defined tissue-specific conditions, including for understanding underlying mechanisms, defining therapeutic targets and conducting compound screening, and the like.

Furthermore, those of ordinary skill in the art will appreciate that the methods, compositions (e.g., tissue grafts), and devices (e.g., bioreactors), described herein can be used in, or in conjunction with, a variety of different model systems and screening methods.

Vascularized Bone Grafts

In one embodiment, the present invention provides a method of preparing a vascularized bone graft, comprising: (a) obtaining a three-dimensional model of a bone portion; (b) partitioning the three-dimensional model of step (a) into two or more bone segment models; (c) preparing two or more bone graft segments, comprising: (i) obtaining a scaffold having a size and shape corresponding to each of the bone segment models of step (b); (ii) obtaining a bioreactor having an internal chamber configured to hold the scaffold; (iii) applying to the scaffold (1) bone-forming cells, or cells capable of differentiating into bone-forming cells, and (2) blood vessel-forming cells, or cells capable of differentiating into blood-vessel forming cells; (iv) culturing the cells on the scaffold within the bioreactor to form a bone graft segment; and (v) removing the bone graft segment from the bioreactor; and (d) assembling the two or more bone graft segments prepared in step (c) to form a bone graft having a size and shape corresponding to the bone portion of step (a). In one embodiment, the cells applied to the scaffold in (c) (iii) comprise pluripotent cells, induced pluripotent cells, progenitor cells, differentiated cells, or any combination thereof. In one embodiment, the cells of (c) (iii) (1) comprise bone marrow stromal cells or mesenchymal stem cells or pluripotent cells induced toward mesenchymal lineage or differentiated bone cells or any combination thereof. In one embodiment, the cells of (c) (iii) (2) comprise endothelial progenitor cells or pluripotent cells induced toward endothelial lineage or differentiated endothelial cells or any combination thereof. In one embodiment, the bone graft segment has a thickness of about one centimeter or less. In one embodiment, the bone graft segment has a thickness of about 0.3 millimeters to about 10 millimeters. In one embodiment, the assembling of the bone graft segments is carried out with an adhesive, one or more pins and holes, or both. In one embodiment, the pins are metallic or resorbable. In one embodiment, the pins are titanium. In one embodiment, the adhesive is a biocompatible bone glue, for example, a polymer such as NOVOSORB® (PolyNovo Biomaterials, Melbourne) or any gel, liquid, rubber-like substance or any other biocompatible material capable of securing together two or more bone segments. Examples of bone glues include, but are not limited to, polymer based bone glues such as polyurethane-based and polymethylmethacrylate-based bone glues. In one aspect, the invention provides a method of repairing or replacing a bone portion in a subject, comprising steps (a)-(d) described above, and further comprising transplanting the bone graft into a subject so as to repair or replace the bone portion in the subject.

In one aspect, the invention provides a vascularized bone graft prepared by a method of the invention utilizing a bioreactor as described herein. In another aspect, the invention provides a vascularized bone graft for repairing or replacing a bone portion in a subject, wherein the bone graft comprises two or more bone graft segments, wherein the two or more bone graft segments are connected together to form a vascularized bone graft having a size and shape corresponding to the bone portion to be replaced or repaired. In some embodiments, the bone graft segments comprise bone cells derived from progenitor cells (such as mesenchymal progenitor cells), pluripotent cells (such as induced pluripotent stem cells), autologous cells (such as the subject's own cells), or any cell capable of (i) forming bone, or (ii) differentiating into a cell that is capable of forming bone. In some embodiments, the bone graft segments comprise endothelial or blood vessel cells derived from progenitor cells (such as endothelial progenitor cells), pluripotent cells (such as induced pluripotent stem cells), autologous cells (such as the subject's own cells), or any cell capable of (i) forming endothelium and/or blood vessels, or (ii) differentiating into a cell that is capable of forming endothelium and/or blood vessels. In some embodiments, each bone segment has a maximum thickness of less than about one centimeter, or has a maximum thickness of about 0.3 millimeters to about 10 millimeters.

In some embodiments the cells used in accordance with the above methods, or used in the manufacture of the above bone grafts, are derived from, or derived from a cell obtained from, the same subject into which the bone graft is to be placed such that they are autologous cells, or are derived from autologous cells. In one embodiment, the cells are derived from pluripotent stem cells, such as, for example, induced pluripotent stem cells, embryonic stem cells, cloned stem cells, or adult stem cells (such as bone marrow stem cells). In some embodiments the induced pluripotent stem cells may be derived from a somatic cell taken from the same subject into which the bone graft is to be placed or from a suitably matched donor, such as HLA-matched. In some embodiments, the cells are mesenchymal stem cells and/or endothelial progenitor cells. In some embodiments, the cells are seeded onto the scaffold at a cell ratio of 1:1, or any ratio from about 2:8 to about 8:2.

The following examples are provided to further illustrate the advantages and features of the present invention, but are not intended to limit the scope of the invention. While they are typical of those that might be used, other procedures, methodologies, or techniques known to those skilled in the art may alternatively be used.

EXAMPLES

Example 1

Use of Bioreactors and Scaffolds to Engineer Large Bone Grafts

Figure 14:
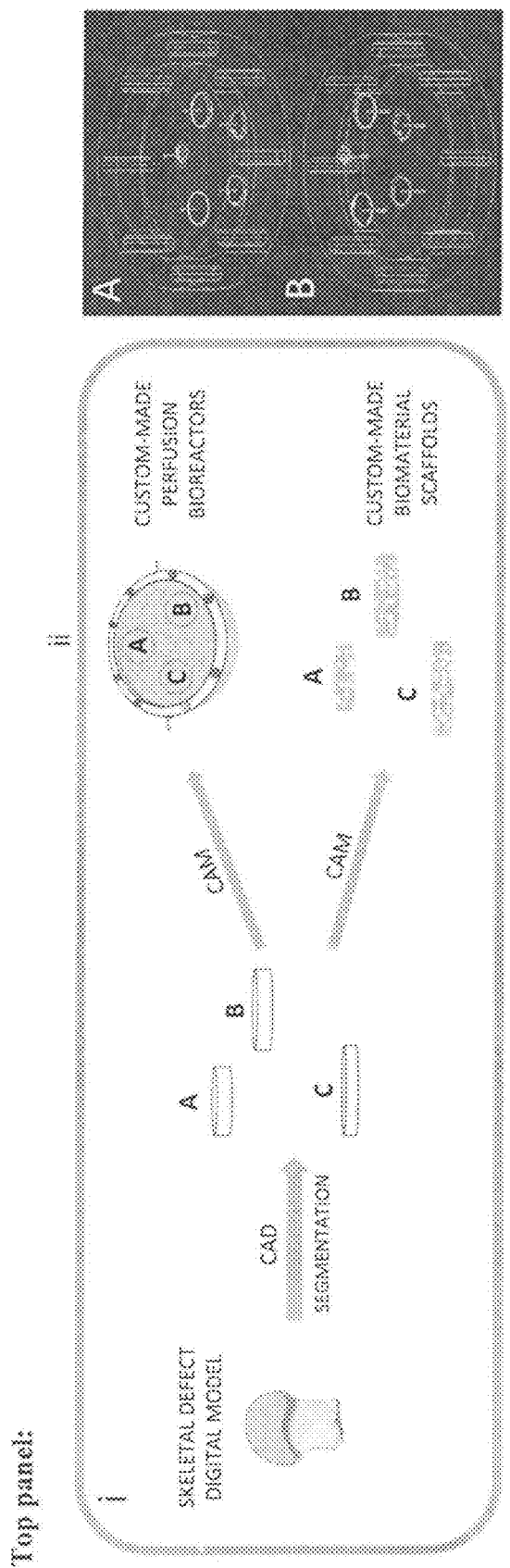
FIG. 14. Top panel: (i) Digital models of skeletal defects are created, segmented (here, into three segments labeled A, B and C) and used to fabricate custom-made biomaterial scaffolds and bioreactors; (ii) Example of the top portion (A) and bottom portion (B) of a perfusion bioreactor created using CAD software. Middle panel: Osteogenic and vascular progenitors are generated from hiPSC and co-cultured onto custom-made osteoinductive scaffolds (here, on three scaffolds labeled A, B and C) in perfusion bioreactors. Bottom panel: Engineered vascularized bone segments (here, three segments labeled A, B and C) are assembled using biocompatible bone glues and/or reinforced using 3D printed titanium pins and holes.
Figure 14:
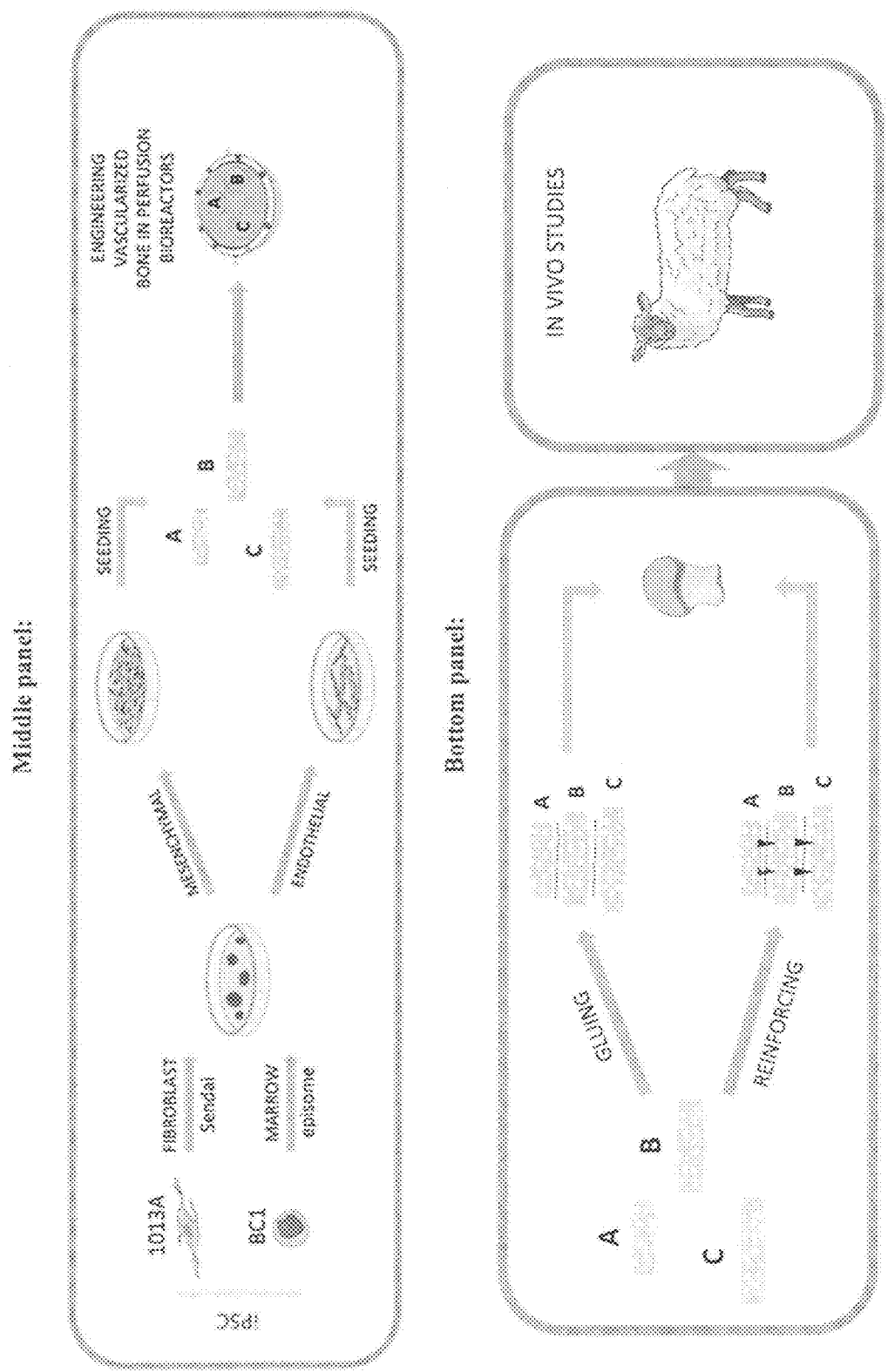

Computed tomography is used to generate anatomically accurate 3D models of traumatic or pathological skeletal defects. Digital models of skeletal defects are then edited using computer-aided design (CAD), and sliced off into pieces of adequate thickness, which allow effective engineering of functional bone tissue using perfusion bioreactors. The partitioned bone defect files are thus imported in computer-aided manufacture (CAM) software to drive the fabrication of geometrically defined biomaterial scaffolds using a combination of computer-controlled milling, rapid prototyping and casting technologies. The partitioned bone defect files are also used to drive the computer-controlled milling or 3D printing of customized perfusion bioreactors that can accommodate the cell/scaffold construct in a press-fit fashion under direct perfusion conditions (see FIG. 14, top panel). Patient-specific bone and blood vessel forming cells are then seeded onto the produced scaffolds, and the cell/scaffold constructs cultured in the relative perfusion bioreactor chambers until maturation of functional vascularized bone tissue (see FIG. 14, middle panel). Engineered bone segments are then assembled to match the shape of the skeletal defect by means of a biocompatible bone glue for welding large bone grafts, and/or reinforced using 3D printed metallic or resorbable pins that integrate and create a stable bond with bone. Following assembling of the segments, the engineered bone grafts is anchored to the host tissues using a similar approach based on biocompatible bone glue and pins resulting in personalized reconstruction of skeletal defects (see FIG. 14, bottom panel).

Example 2

Computer-Aided Design and Manufacture of Bioreactors and Scaffolds

Bioreactors and scaffolds provided by the invention can be designed and manufactured as described herein. In some embodiments, computer-aided design (CAD) and computer-aided manufacture (CAM) are used to design and manufacture the bioreactors and/or scaffolds. A person having ordinary skill in the art will appreciate that any other methods of designing and manufacturing may be used to generate bioreactors and/or scaffolds according to the present invention.

Digital models of skeletal defects can be created using CAD software, e.g., AUTOCAD®, SOLIDWORKS®, PROE®, and CREO®. Reference models of skeletal defects in CAD can be edited and segmented into smaller complementary sub-parts which represent bone segments that can be cultured in perfusion bioreactors without affecting the perfusion system. The segmented bone sample files can be saved in compatible formats, for example, IGES or SLT formats, and imported in CAM software (e.g., SPRUT-CAM®).

The segmented bone sample files edited in CAD can be used to design a customized bioreactor, which is of suitable size and shape to accommodate a scaffold construct in a press-fit fashion under direct perfusion conditions. The CAD files are converted into compatible formats and imported into CAM and/or 3D printer software, and used to fabricate the bioreactors using different plastic materials.

The generated files in CAM software can be processed to generate the appropriate G-Codes to drive a computer-numerical-control (CNC) milling machine (for example, Tormach, Bridgeport) and to select appropriate machining tools bits and program the machining paths to cut the scaffolding materials into the desired segmented shapes. For example, plugs of trabecular bone (cow and/or human) of adequate size can be drilled, cleansed under high-pressure streamed water to remove the bone marrow, and then sequentially washed to remove cellular material. Decellularized bone plugs will then be freeze-dried, and used for the fabrication of scaffolds corresponding to the shape and size of the segmented samples of the skeletal defect. The invention provides scaffolds made of synthetic, resorbable and/or mechanically compliant ceramic/polymer composite materials. The efficient manufacture of scaffolds is important for the reproducible and large-scale fabrication of bone substitutes for clinical applications.

Example 3

Engineering Vascularized Bone Grafts for Repairing Large Skeletal Defects

Introduction

This Example proposes a strategy for engineering vascularized bone grafts from human induced pluripotent stem cells (hiPSCs) for enhanced healing of complex skeletal defects. In particular, the ability to derive autologous osteogenic and vascular cells constituting healthy bone from hiPSCs for any patient in virtually unlimited numbers represents an unprecedented therapeutic resource. Vascularized bone substitutes will be engineered using a biomimetic scaffold-bioreactor approach to bone development. Computer-aided and rapid prototyping technologies will allow the preparation of bone substitutes of any shape and size. Digital models of large bone defects will be created and then segmented in complementary sub-parts that will be used to produce customized biomaterial scaffolds and bioreactors via computer-aided design and manufacturing technologies, such as 3D printing (see FIG. 14). The proposed engineering strategy overcomes the limitations associated with perfusion culture of large bone grafts. Mesenchymal and endothelial progenitor cells will be derived from hiPSCs generated using any available reprogramming method, and then combined with compliant scaffolds and cultured in perfusion bioreactors until maturation of functional vascularized tissue (see FIG. 14). Engineered bone segments will then be assembled together (lego-like approach) using a biocompatible bone glue, and/or reinforced using 3D printed titanium holes and pins to match the shape and dimension of the original defect. Future studies will be aimed at exploring the therapeutic potential of hiPSC-engineered bone using different animal models of complex skeletal defects (see FIG. 14).

Engineering large and geometrically defined vascularized bone grafts from hiPSCs represents a novel solution for the treatment of skeletal defects characterized by severe bone loss, and opens the opportunity to provide personalized therapies to a large number of patients. As importantly, such bone grafts represent qualified models to study bone development and pathologies, as well as screening new drugs and test biomaterials.

This Example describes studies designed to engineer vascularized bone grafts from human induced pluripotent stem cells (hiPSC) for enhanced healing of skeletal defects. Patient-specific bone grafts will be engineered using a biomimetic scaffold-bioreactor approach of bone development in vitro, and customized to meet specific clinical needs with the aid of computer-assisted and rapid prototyping technologies. Engineering patient-specific customized bone grafts could be used to develop innovative treatments to restore skeletal integrity and functionality in clinical situations characterized by severe bone loss.

This Example proposes studies to engineer vascularized bone substitutes from hiPSCs, and adopt a combination of medical imaging procedures, computer-aided technologies and rapid prototyping to allow the construction of clinically relevant bone substitutes in perfusion bioreactors of the present invention. The strategy represents a novel and innovative solution to cope with the burden of bone deficiencies, whose clinical translation will have profound social impact by improving the health status and quality of life of many patients. These studies will also provide new insights into hiPSC biology, which are critical to understand functional differentiation of pluripotent stem cells into mature tissues and organs. Additionally, hiPSC-engineered vascularized bone grafts would provide valuable high-fidelity models to investigate tissue development in normal and pathological conditions, and test new pharmaceuticals and biomaterials within a context that resembles several aspects of the native bone environment.

Background

Bone displays intrinsic capacity to regenerate and self-repair but this ability is limited to small fractures and reconstructive therapies are needed in a large number of clinical conditions to restore tissue integrity and functionality. Current treatments are based on the transplantation of autogenic and/or allogeneic bone grafts, or implantation of graft materials with osteoconductive and osteoinductive properties. Autogeneic bone grafts represent the gold standard treatment for bone replacement procedures, due to immune tolerability and provision of essential components supporting bone regeneration and repair, but limited availability and donor site morbidity often restrict their clinical use. On the other hand, allogeneic decellularized bone grafts are available in large amounts but integrate slowly, carry the risk of infection transmission and may display immune incompatibility leading to transplant rejection. Implantation of alloplastic materials overcomes some of the restrictions encountered with autogenic and allogeneic grafts, including disease transmission, complex shape and availability, but display poor integration, frequently result in biomaterial-associated infection, and lack biological functionality and mechanical compliance, leading to implant failure and substitution. Bone tissue engineering represents a promising therapeutic solution, since it opens the possibility to engineer an unlimited amount of viable bone substitutes to meet specific clinical needs. Human mesenchymal stem cells (hMSC) derived from adult tissues have been extensively used for bone engineering applications with encouraging results, but exhibit restricted potential for clinical applications due to limited availability, inadequate regenerative potential and decrease in functionality associated with in vitro expansion and donor age.

Autologous bone substitutes in the size range of ~1 cm have been grown from adult stem cells and used to facilitate bone healing in experimental animals and in humans. However, their scale-up to clinical sizes and functionality are limited due to the lack of blood supply, and limited proliferation and vasculogenic potential of cultured adult stem cells. An appropriate blood supply has been recognized as an essential component of normal fracture healing and defective angiogenesis at the fracture site has been a primary consideration when poor outcomes occur. Poor blood supply leads to hypoxia and necrosis of the grafted tissue, and can result in decreased bone formation ("atrophic bone"). Similarly, implantation of large cellularized bone substitutes without the connection to vascular supply can result in cell death in the interior regions of the transplant. To expedite cell survival and bone regeneration, recent tissue engineering approaches have involved transplantation of endothelial progenitors or vascular networks within bone substitutes. Studies have shown the positive effects of endothelial cells and osteogenic cells in direct co-culture model. In addition, studies suggest that co-transplantation of endothelial cells and BMSC promoted new bone formation in vivo, and that endothelial networks engineered within bone substitutes can functionally anastomose with the host vasculature.

Pluripotent stem cells display high regenerative potential and ability to differentiate toward all specialized cells constituting healthy bone tissue. When derived using nuclear reprogramming technologies, pluripotent stem cells allow the construction of patient-specific bone substitutes for personalized applications. Both mesenchymal and endothelial progenitor cells have recently been derived from pluripotent stem cells, opening new opportunities for the unlimited construction of vascularized bone substitutes for enhanced reconstructions of large skeletal defect. It is therefore important to explore the possibility to engineer vascularized bone grafts from induced pluripotent stem cells, in order to develop safe and effective treatments for many patients affected by severe skeletal defects and bone disorders.

Results

The inventors have extensive experience with cultivation of bone substitutes from mesenchymal stem cells derived from adult tissues and from human pluripotent stem cells. A set of studies exploring the relative regenerative potential of hMSCs and mesenchymal progenitors derived from human embryonic stem cell (hESC) lines have demonstrated comparative advantages of hESC-derived mesenchymal progenitors for bone engineering applications. Studies in monolayer and 3D cultures on scaffolds in bioreactors have shown that hESC-derived mesenchymal progenitors highly resemble hMSCs in terms of morphology, surface antigen and global gene expression profile, but display higher proliferation potential, biosynthetic activity and mineralization properties, all paramount features for the unlimited construction of functional substitutes for bone engineering applications. The derivation protocol has been extended to hiPSC lines generated from different tissues and using different reprogramming technologies based on non-integrating vectors, opening the possibility to engineer safe patient-specific bone substitutes for personalized applications. hiPSC lines were characterized by immunohistochemistry to assess pluripotency and karyotyped, before being induced toward the mesenchymal lineage for 7 days. Mesenchymal-like phenotype was characterized by flow cytometry and by probing surface marker expression and differentiation potential in monolayer (osteogenesis, adipogenesis) and pellet cultures (chondrogenesis). Differentiation toward the osteogenic lineage was confirmed by alkaline phosphatase and mineralization, differentiation toward the chondrogenic lineage was shown by glycosaminoglycans, and differentiation toward the adipogenic lineages was shown by lipid characterization.

Cells were then seeded on decellularized bone scaffolds (4 mm Ø×4 mm height), and cultured in osteogenic medium under constant perfusion (linear flow velocity of 800 µm/sec) for 5 weeks before 12-week subcutaneous implantation in immunocompromised mice to assess stability and further tissue maturation. Histological and immunohistochemical analyses of engineered bone were carried out following bioreactor cultivation and subcutaneous implantation in immunocompromised mice. Micrographs showed maturation of phenotypically stable bone-like tissue and vascularization. MicroCT analysis of engineered bone showed an increase in mineral density and structural parameters.

Altogether the results demonstrate that mesenchymal progenitors can be derived from hiPSC lines, and used to engineer mature and phenotypically stable bone tissue for repair treatments of skeletal defects in personalized applications. In all studies, perfusion bioreactors were shown to be particularly important for bone development, as they provide biomechanical stimulation to the cells, and support survival of the cells in the interior of the constructs, resulting in the production of thick homogenous bone-like matrix. Studies are now directed at developing suitable protocols for engineering vascularized bone substitutes for enhanced healing of large and geometrically complex skeletal defects. Preliminary studies have shown that functional endothelial progenitors can be derived from hESC lines. Following differentiation of embryoid bodies in controlled conditions, isolated CD34 positive cells were able to specifically internalize DiI-Ac-LDL and form tubes when plated on Matrigel. This approach is being translated to hiPSCs for the construction of patient-specific multicellular composite bone substitutes.

In addition, preliminary vascularization studies in 3D cultures have shown that co-culture of hiPSC-derived mesenchymal progenitors and human bone marrow stromal cells (BMSC) with human umbilical vein endothelial cells (HUVEC) result in long-lasting formation of vascular networks, both when cells are embedded in fibrin clots or seeded onto decellularized bone scaffolds, which represent more compliant substrates for skeletal repair treatments. Interestingly, number and stability of vascular structures were similar when HUVEC were cultured with hiPSC-derived mesenchymal progenitors and human BMSC in fibrin clots. Epifluorescence micrographs showed the presence of stable 3D vascular networks 3 weeks after seeding. Hematoxylin/Eosin staining of clot cross sections showed the presence of hollow vessels across the entire construct for both co-culture of mesenchymal progenitors derived from hiPSC line 1013A and BMSC with HUVEC 4 weeks after seeding. To follow the formation of vascular network in vitro, cell populations were specifically labeled with different VYBRANT® tracker dyes before embedding in fibrin clots, and cultured for 4 weeks in a mixture of osteogenic and endothelial inducing media before harvesting for histological analysis. No vascular structures were observed when HUVEC were cultured alone, suggesting the pivotal role of mesenchymal cells to support and guide tissue vascularization. Studies can be carried out to identify the molecular mechanism underlying this finding in order to develop improved protocols to support maturation of vascularized bone tissue in vitro.

Similar outcomes were observed when cells were seeded onto decellularized bone scaffolds (8 mm Ø×2 mm height) and cultured for 6 weeks under osteogenic- and vascular-inducing conditions. The maturation of bone-like tissue, evidenced by the positive staining for osteocalcin, osteopontin and bone sialoprotein, was accompanied by the formation of networks of hollow vessels inside the constructs. Immunohistochemical examination showed that the tubular structures were positive for the endothelial marker CD31.

Different seeding ratios, and culture conditions can be tested to explore the potential to enhance the formation of vascularized bone tissue, as well as to assess the potential of other hiPSC lines for engineering vascularized bone grafts. Future studies are aimed at exploring the effect of dynamic conditions in perfusion bioreactors on the vascularization process. Development of proper vascularization protocols, in combination with the biomimetic osteoinductive scaffold-perfusion bioreactor approach, will allow the construction of vascularized bone grafts for personalized repair treatments of complex skeletal defects.

Research Design and Methods

This Example proposes the engineering of vascularized bone grafts from hiPSCs using a stepwise differentiation approach, starting with derivation of lineage-specific osteogenic and endothelial progenitors, and subsequent co-culture of these progenitors in a "biomimetic" scaffold-bioreactor system, which ensure controlled development of functional bone tissue in vitro. Computer-aided and rapid prototyping technologies will be employed to enable the fabrication of custom-made bone substitutes for the reconstruction of large and geometrically complex skeletal defects. Engineering patient-specific custom-made bone grafts can be used to develop innovative treatments to restore skeletal integrity and functionality in clinical situations characterized by severe bone loss. This Example describes three sub-projects as described below.

1: Computer-Aided Design (CAD) of Skeletal Models and Computer-Aided Manufacturing (CAM) of Biomaterial Scaffolds and Perfusion Bioreactors.

The objective of Part 1 is to create and elaborate digital models of skeletal defects to guide the design and manufacturing of customized biomaterial scaffolds and perfusion bioreactors. Digital models of skeletal defects will be created and segmented into complementary sub-parts using CAD software, then these models will be used as a reference for the computer-aided fabrication of biomaterial scaffolds of corresponding size and shape and custom-made perfusion bioreactors. Bioreactors will be machined and/or free-form fabricated using the digital models in order to accommodate each specific cell/scaffold construct in a press-fit fashion and allow culture under direct perfusion.

Digital models of skeletal defects will be created using CAD software (e.g., AUTOCAD®, SOLIDWORKS®, PROE®, PROE®). To validate the therapeutic potential of the proposed engineering strategy, this approach can be extended to defect models of different size and shape. Reference models of skeletal defects in CAD will be edited and segmented into smaller complementary sub-parts (lego-like building parts) that can be cultured in perfusion bioreactors without affecting the perfusion system. The segmented bone sample files will then be saved in compatible IGES or SLT formats and imported in CAM software (e.g., SPRUTCAM®). The generated files in CAM software will then be processed to generate the appropriate G-Codes to drive a computer-numerical-control (CNC) milling machine (e.g., Tormach, Bridgeport), select appropriate machining tools bits and program the machining paths to cut the scaffolding materials into the desired segmented shapes. Plugs of trabecular bone (cow and/or human) of adequate size will be drilled, cleansed under high-pressure streamed water to remove the bone marrow, and then sequentially washed to remove cellular material as previously described (41). Decellularized bone plugs will then be freeze-dried, and used for the fabrication of scaffolds corresponding to the shape and size of the segmented samples of the skeletal defect. The potential to use synthetic, resorbable and mechanically compliant ceramic/polymer composite materials will be explored in parallel, since it represents an essential requisite for the reproducible and large-scale fabrication of bone substitutes for clinical applications. Fabricated scaffolds will be sterilized and conditioned in culture medium overnight prior to cell seeding. The segmented bone sample files edited in CAD will then be used to design customized bioreactor, which can accommodate the cell/scaffold construct(s) in a press-fit fashion under direct perfusion conditions. Again, the CAD files will be converted into compatible formats and imported into CAM and/or 3D printer software, and used to fabricate the bioreactors using different plastic materials. Each bioreactor will be constituted of two parts (top and bottom) that will be secured together, for example, by means of metallic screws. The cell/scaffold constructs will be cultured in between the top and bottom elements. The bottom part will include key elements including but not limited to the inlet port and channels for flow perfusion, as well as anatomically shaped chambers to accommodate the cell/scaffold constructs. The top part will include elements such as a medium reservoir and the outlet port for flow perfusion. A system of tubes can be used to connect the inlet and outlet ports and allow perfusion throughout the bioreactors via the control of a peristaltic pump.

2: Engineering Vascularized Bone in Custom-Made Perfusion Bioreactors.

The objective of Part 2 is to engineer vascularized patient-specific bone grafts in vitro. hiPSC lines reprogrammed from different tissues using non-integrating vectors will be induced toward the mesenchymal and endothelial lineage prior to culture under biomimetic conditions in the osteoinductive scaffold-perfusion bioreactor system as described herein to guide maturation of functional vascularized bone tissue.

hiPSC reprogrammed using non-integrating vectors from different donors and source tissues (line BC1 and 1013A) will be expanded, characterized for pluripotency and karyotyped before induction toward the mesenchymal and endothelial lineages. Derived progenitor cells will be expanded, characterized by flow cytometry, and karyotyped to assess genetic normality. Qualitative and quantitative methods will be used to evaluate osteogenic and endothelial phenotype in vitro, including histological and immunohistochemical examination, biochemical and morphological assays, and gene expression analysis. Vascular induction will be tested in monolayer cultures and embryoid bodies, in the presence of specific factors (BMP-4, activin, bFGF, VEGF). Differentiated progenitors will be sorted based on surface antigen expression (CD34, CD31, KDR, C-KIT) and cultured in endothelial media. Progenitor yield, viability, proliferation and phenotype—expression of specific markers (CD31, vWF, VE-cadherin, SMA) will be assessed by flow cytometry, immunofluorescence and gene expression. Network formation and sprouting will be tested by encapsulation in collagen/fibronectin/Matrigel before co-cultivation studies. Commercially available BMSC (Lonza) and HUVEC (Lonza) will be used as reference lines to assess the quality and functionality of hiPSC-derived mesenchymal and endothelial progenitors. To engineer vascularized bone tissue, hiPSC-derived mesenchymal and endothelial progenitors will be co-seeded onto decellularized bone scaffolds (or others) and cultured in bioreactor in a mix of osteogenic and endothelial medium. Pre-differentiation, cell seeding ratios, concentration of differentiation factors and use of fibrin sealants will be explored to design optimal culture conditions for the development of fully vascularized bone grafts in vitro. Culture in bioreactors will be conducted for a period of 3-5 weeks, until the formation of a mature vascularized tissue. Tissue development will be assessed using qualitative and quantitative methods, including histological and immunohistochemical examination, biochemical assays, high-resolution characterization techniques (SEM, FIB-TEM, Tof-SIMS), imaging procedures (microCT) and mechanical testing (Young's modulus, tensile and compressive strength).

3: Gluing of Engineered Bone Segments and Evaluation of Stability.

The objective of Part 3 is to fabricate custom-made bone grafts for complex skeletal reconstruction. Engineered vascularized bone segments will be assembled to match the shape of the skeletal defect by means of a biocompatible bone glue, or reinforced using 3D printed metallic (for example, titanium) or resorbable pins and holes. Future studies will be aimed at exploring safety and efficacy of engineered bone in animal models of critical-sized skeletal defects (both in loading and non-loading anatomical locations).

Engineered bone segments will be assembled to match the shape of the model of skeletal defect by means of a biocompatible bone glue for welding large bone grafts or reinforced using 3D printed metallic (for example, titanium) or resorbable pins and holes. Future studies will be aimed at exploring the safety and regenerative potential of engineered bone in animal models of complex critical sized skeletal defects (both in loading and non-loading skeletal locations). For example, digital models of femoral head defects in adult animals will be created using medical imaging procedures (CT scan) and 3D images processed and segmented (as described above) and used to engineer vascularized bone as described herein. Femoral head ostectomy will then be performed in the animals to remove the femur head to an extent matching the digital model generated (as described above), and the engineered vascularized bone placed in site to restore skeletal integrity and functionality. Tissue development, healing and quality of regenerated tissue will be evaluated in vivo using medical imaging procedures and following explanation using histological and immunohistochemical techniques, high-resolution characterization techniques (e.g., SEM, FIB-TEM, Tof-SIMS), and mechanical testing (e.g., Young's modulus, tensile and compressive strength).

As described herein, vascularized bone grafts can be engineered using osteogenic and endothelial progenitors derived from human induced pluripotent stem cells for personalized reconstructive therapies. Although endothelial progenitors can be derived from both hESCs and hiPSCs (38-40), the derivation efficiency is low and the derived progenitors display scarce proliferation ability, which limits the possibility to generate enough cells for engineering large vascularized bone substitutes. To speed up the development of suitable vascularization protocols, in parallel to optimizing the derivation of highly proliferative endothelial progenitors from hiPSCs, commercially available HUVECs can be used, and then the protocols can be translated to endothelial progenitors derived from hiPSCs. The hiPSC-derived mesenchymal progenitors may be expanded to a required amount before induction toward the endothelial lineage, and then used to engineer vascularized bone substitutes.

As described herein, the engineered bone substitutes can be assembled to match the shape of the skeletal defect using a biocompatible bone glue for welding large bone grafts, which might be insufficient to ensure a stable connection following implantation in high load-bearing locations. To solve this problem, alternative solutions will be tested, including reinforcement using 3D printed metallic or resorbable pins and holes.

Human Stem Cells

A stepwise protocol is proposed for preparation of vascularized bone grafts from hiPSCs, which will include: (a) Differentiation and expansion of osteogenic and vascular progenitors from hiPSCs, and testing their functional potential for new tissue formation; (b) Preparation and seeding of decellularized bone scaffolds or any other biocompatible and resorbable biomaterial scaffolds; and (c) Cultivation of osteogenic tissue phase in conjunction/sequence with formation of microvascular network.

Cell lines: hiPSC lines 1013A (derived by Sendai virus in the NYSCF laboratory) and BC1 (derived by episomal plasmid vector, from Life Technologies) can be used. Initial studies will be done in parallel with ESC line H9 (from Wicell Research Institute) and commercially available adult cells (BMSC and HUVEC from Lonza).

The data generated from this protocol are expected to provide a proof of concept for development of vascularized bone substitutes from hiPSC utilizing bioreactors as described herein.

Although the invention has been described with reference to the above example, it will be understood that modifications and variations are encompassed within the spirit and scope of the invention. Accordingly, the invention is limited only by the following claims.

What is claimed is:

1. A perfusion bioreactor suitable for use in the preparation of a tissue graft segment comprising:
   a) a graft chamber comprising a graft chamber floor;
   b) an equilibration chamber adjacent the graft chamber and in fluid communication with the graft chamber, wherein the equilibration chamber comprises an equilibration chamber floor having a fluid opening opposing the graft chamber and in fluid communication with an inlet; and
   c) an outlet disposed downstream of the graft chamber and the equilibration chamber, wherein a fluid path is defined between the inlet and the outlet whereby fluid flows through the graft chamber and the equilibration chamber from the fluid opening to the outlet, and wherein the bioreactor is configured such that fluid enters into the equilibration chamber generally perpendicular to the equilibration chamber floor and the graft chamber floor.

2. The perfusion bioreactor of claim 1, wherein the graft chamber is configured to accommodate a tissue graft segment.

3. The perfusion bioreactor of claim 1, wherein the graft chamber further comprises a graft chamber insert configured to accommodate a tissue graft segment.

4. The perfusion bioreactor of claim 3, wherein the graft chamber insert is custom-designed to accommodate the tissue graft segment.

5. The perfusion bioreactor of claim 3, wherein the graft chamber insert is custom-designed to accommodate the tissue graft segment using a digital three-dimensional model of the tissue graft segment.

6. The perfusion bioreactor of claim 5, wherein the digital three-dimensional model of the tissue graft segment is generated by medical imaging, computed tomography, computer-assisted design, or any combination thereof.

7. The perfusion bioreactor of claim 1, comprising a bottom portion and a top portion, the bottom portion comprising: i) the graft chamber, ii) the equilibration chamber, iii) the inlet, and iv) a fluid channel between the inlet and the equilibration chamber.

8. The perfusion bioreactor of claim 7, wherein the bottom portion and top portion are formed as a single unitary piece.

9. The perfusion bioreactor of claim 7, wherein the top portion comprises: i) a fluid reservoir, ii) an aperture fluidly connecting the fluid reservoir and the graft chamber, and iii) the outlet.

10. The perfusion bioreactor of claim 9, wherein the bottom and top portions are attached via a fastening mechanism.

11. The perfusion bioreactor of claim 10, wherein the fastening mechanism comprises screws, rods, pins, clips, latches or any combination thereof.

12. The perfusion bioreactor of claim 10, wherein the top and bottom portions further comprise one or more holes to facilitate the fastening mechanism.

13. The perfusion bioreactor of claim 10, further comprising a sealing mechanism situated between the top and the bottom portions.

14. The perfusion bioreactor of claim 10, further comprising a sealing device capable of preventing fluid leakage from between the bottom and top portions.

15. The perfusion bioreactor of claim 14, wherein the sealing device is an o-ring.

16. The perfusion bioreactor of claim 1, further comprising a fluid pump and one or more tubes fluidly connecting the inlet and the outlet to the pump thereby providing a fluid circuit.

17. The perfusion bioreactor of claim 16, wherein the pump is a peristaltic pump.

18. The perfusion bioreactor of claim 1, wherein the graft chamber is custom-designed to accommodate the tissue graft segment.

19. The perfusion bioreactor of claim 1, wherein the graft chamber is custom-designed to accommodate the tissue graft segment using a digital three-dimensional model of the tissue graft segment.

20. The perfusion bioreactor of claim 19, wherein the digital three-dimensional model of the tissue graft segment is generated by medical imaging, computed tomography, computer-assisted design, or any combination thereof.

21. The perfusion bioreactor of claim 1, wherein the tissue graft segment has a maximum thickness of about one centimeter or less.

22. The perfusion bioreactor of claim 1, wherein the tissue graft segment has a maximum thickness of about 0.3 millimeters to 10 millimeters.

23. The perfusion bioreactor of claim 1, wherein the equilibration chamber further comprises one or more diffusion enhancing elements.

24. The perfusion bioreactor of claim 1, wherein the equilibration chamber further comprises an insert to maintain the dimensions of the equilibration chamber and/or maintain fluid flow through the perfusion bioreactor.

25. The perfusion bioreactor of claim 1, wherein the graft chamber further comprises an insert to (i) maintain the size and dimensions of the graft chamber and equilibrium chamber, and/or (ii) maintain fluid flow through the perfusion bioreactor.

* * * * *